United States Patent
Wang et al.

(10) Patent No.: US 9,758,566 B2
(45) Date of Patent: Sep. 12, 2017

(54) RECOMBINANT CYTOTOXIC T-LYMPHOCYTE-ASSOCIATED PROTEIN 4 (CTLA4)

(71) Applicant: The General Hospital Corporation, Boston, MA (US)

(72) Inventors: Zhirui Wang, Malden, MA (US); David H. Sachs, Newton, MA (US); Christene A. Huang, Dover, MA (US)

(73) Assignee: The General Hospital Corporation, Boston, MA (US)

( * ) Notice: Subject to any disclaimer, the term of this patent is extended or adjusted under 35 U.S.C. 154(b) by 199 days.

(21) Appl. No.: 14/389,013

(22) PCT Filed: Feb. 28, 2013

(86) PCT No.: PCT/US2013/028196
§ 371 (c)(1),
(2) Date: Sep. 29, 2014

(87) PCT Pub. No.: WO2013/148049
PCT Pub. Date: Oct. 3, 2013

(65) Prior Publication Data
US 2015/0118260 A1 Apr. 30, 2015

Related U.S. Application Data

(60) Provisional application No. 61/617,345, filed on Mar. 29, 2012.

(51) Int. Cl.
*C07K 14/705* (2006.01)
*A61K 38/00* (2006.01)
*C07K 14/21* (2006.01)
*C07K 14/34* (2006.01)

(52) U.S. Cl.
CPC ........ *C07K 14/70521* (2013.01); *C07K 14/21* (2013.01); *C07K 14/34* (2013.01); *A61K 38/00* (2013.01); *C07K 2319/21* (2013.01); *C07K 2319/55* (2013.01)

(58) Field of Classification Search
None
See application file for complete search history.

(56) References Cited

U.S. PATENT DOCUMENTS

| | | |
|---|---|---|
| 5,434,131 A | 7/1995 | Linsley et al. |
| 5,844,095 A | 12/1998 | Linsley et al. |
| 5,851,795 A | 12/1998 | Linsley et al. |
| 5,885,579 A | 3/1999 | Linsley et al. |
| 5,885,796 A | 3/1999 | Linsley et al. |
| 5,968,510 A | 10/1999 | Linsley et al. |
| 5,977,318 A | 11/1999 | Linsley et al. |
| 6,346,248 B1 * | 2/2002 | De Boer .......... A61K 47/48561 424/130.1 |
| 2002/0114814 A1 * | 8/2002 | Gray ............... C07K 14/70503 424/178.1 |
| 2010/0075891 A1 | 3/2010 | Ayalon-Soffer et al. |
| 2011/0287032 A1 * | 11/2011 | Lazar ............... C07K 14/70521 424/178.1 |
| 2015/0051158 A1 * | 2/2015 | Akamatsu ........ A61K 47/48246 514/21.2 |
| 2016/0017018 A1 * | 1/2016 | Wang ............... C07K 14/70521 424/134.1 |

FOREIGN PATENT DOCUMENTS

| | | |
|---|---|---|
| EA | 15860 | 12/2011 |
| RU | 2283847 | 9/2006 |

OTHER PUBLICATIONS

Darlington et al. (J. Immunol. 175 (2), 996-1004 (2005)).*
Peraino et al. (Protein Expression and Purification 82 (2012) 270-278).*
Yokosuka et al. (Immunity (2010) 33: 326-339).*
International Search Report and Written Opinion mailed Jun. 27, 2013 in international application No. PCT/US 2013/028196, 7 pgs.
International Preliminary Report on Patentability in International Application No. PCT/US2013/028196, mailed Oct. 9, 2014, 5 pages.
Bour-Jordan et al., "Intrinsic and extrinsic control of peripheral T-cell tolerance by costimulatory molecules of the CD28/B7 family," Immunol Rev., 2011, 241:180-205 (Author Manuscript).
Brondyk, "Selecting an appropriate method for expressing a recombinant protein," Methods Enzymol., 2009, 463:131-147.
Cho et al., "Establishment of transplantable porcine tumor cells lines derived from MHC-inbred miniature swine," Blood, 2007, 110:3996-4004.
Garin et al., "Urinary CD80 is elevated in minimal change disease but not in focal segmental glomerulosclerosis," Kidney Int., 2010, 78:296-302.
Kim et al., "A fold-back single-chain diabody format enhances the bioactivity of an anti-monkey CD3 recombinant diphtheria toxin-based immunotoxin," Protein Eng. Des. Sei., 2007, 20:425-432.
Larsen et al., "Rational development of LEA29Y (belatacept), a high-affinity variant of CTLA4-Ig with potent immunosuppressive properties," Am J Transplant, 2005, 5:443-53.
Liu et al., "Expression of an anti-CD3 single-chain immunotoxin with a truncated diphtheria toxin in a mutant CHO cell line," Protein Expr. Purif., 2000, 19:304-311.
Peraino et al., "Expression and purification of soluble porcine CTLA-4 in yeast Pichia pastoris," Protein Expr Purif., 2012, 82:270-278 (Author Manuscript).
Riha and Rudd, "CD28 co-signaling in the adaptive immune response," Self Nonself., 2010, 1:231-240.
Rudd et al., "CD28 and CTLA-4 coreceptor expression and signal transduction," Immunol Rev., 2009, 29:12-26 (Author Manuscript).
Sansom, "CD28, CTLA-4 and their ligands: who does what and to whom?" Immunology, 2000, 101:169-177.

(Continued)

*Primary Examiner* — Ilia Ouspenski
(74) *Attorney, Agent, or Firm* — Fish & Richardson P.C.

(57) ABSTRACT

This invention relates to recombinant CTLA-4 proteins, e.g., soluble CTLA-4 or CTLA-4 fusion toxins, and methods for making and using them.

7 Claims, 12 Drawing Sheets

(56) References Cited

OTHER PUBLICATIONS

Figure 5A:
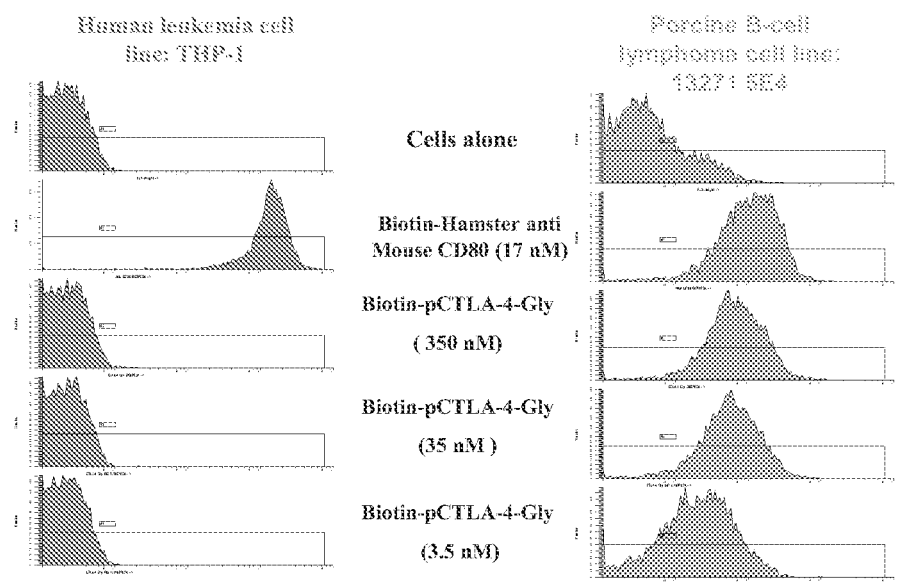

Sreekrishna, K., 1993, "Strategies for optimizing protein expression and secretion in the methylotrophic yeast Pichia pastoris." in Industrial Microorganism: Basic and Applied Molecular Genetics. R. H. Baltz, G. D. Hegeman, and P. L. Skatrud, eds. American Society of Microbiology, Washington, DC, pp. 119-126.

Vaughan et al., "Porcine CTLA4-Ig lacks a MYPPPY motif, binds inefficiently to human B7 and specifically suppresses human CD4+ T cell responses costimulated by pig but not human B7," J Immunol., 2000, 165:3175-3181.

Wang et al., "Development of a Diphtheria Toxin Based Antiporcine CD3 Recombinant Immunotoxin," Bioconjug Chem., 2011, 22:2014-2020 (Author Manuscript).

Wing et al., "CTLA-4 control over Foxp3+ regulatory T cell function," Science, 2008, 322:271-275.

Woo and Neville Jr., "Separation of bivalent anti-T cell immunotoxin from Pichia pastoris glycoproteins by borate anion exchange," BioTechniques, 2003, 35:392-398.

Woo et al., "Gene optimization is necessary to express a bivalent anti- human anti-T cell immunotoxin in Pichia pastoris," Protein Expr. Purif., 2002, 25:270-282.

Yamada et al., "Marked prolongation of porcine renal xenograft survival in baboons through the use of alpha1,3-galactosyltransferase gene-knockout donors and the cotransplantation of vascularized thymic tissue," Nat. Med., 2005, 11:32-34.

Zhu et al., "Molecular cloning, expression and characterization of the functional domain of CTLA4 from the rhesus monkey, Macaca mulatta," Dev Comp Immunol., 2011, 35:736-744.

* cited by examiner

FIG. 1
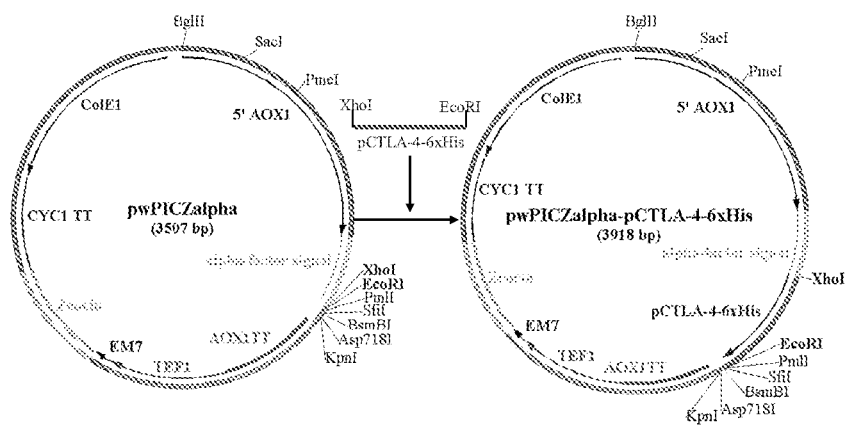
FIGs. 2A-B
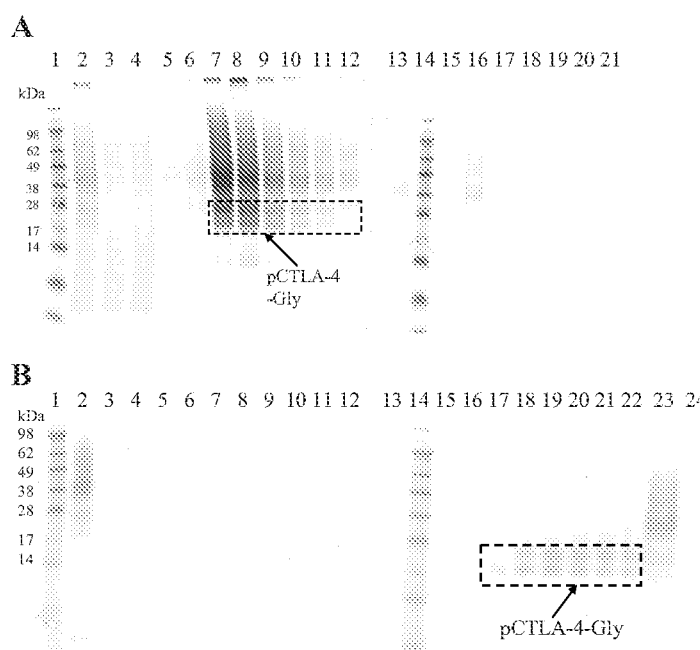

Figs. 3A-B
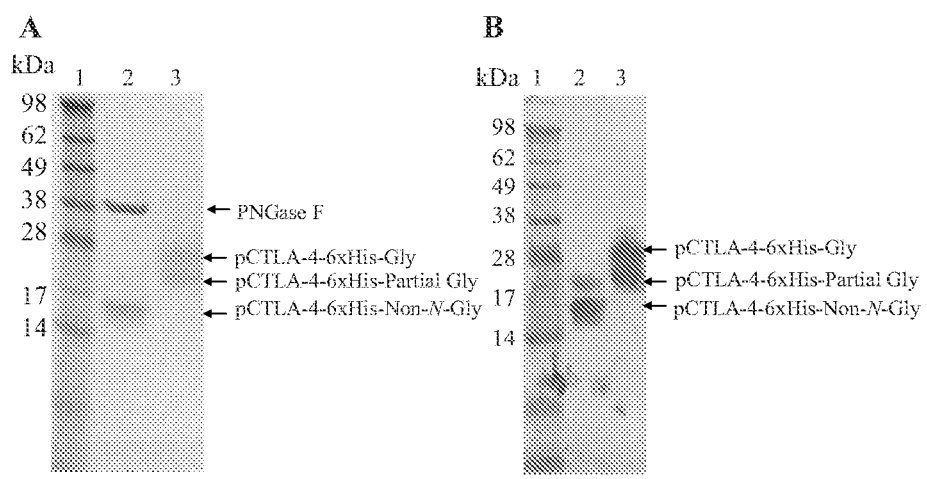

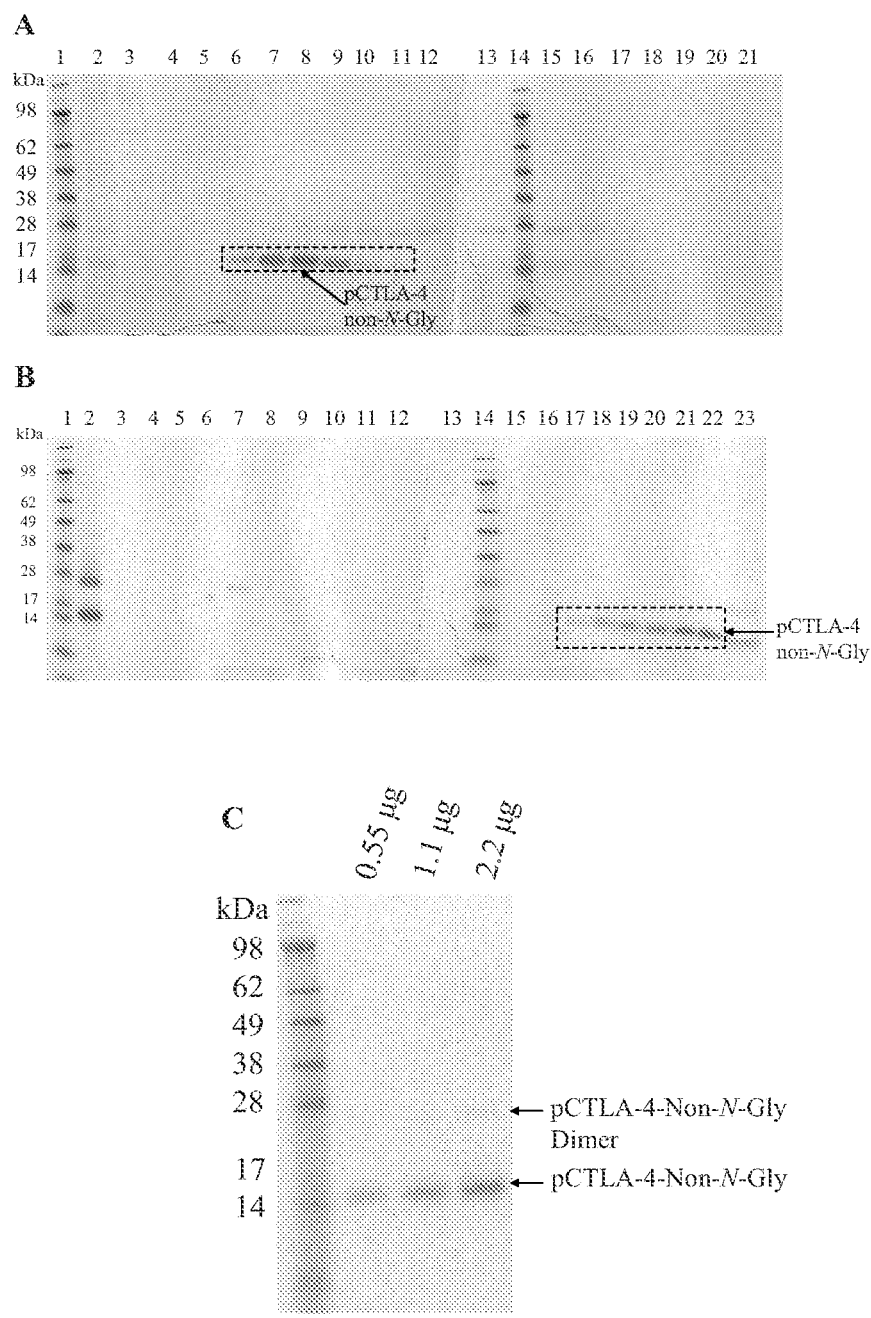

FIGs. 5A-B

FIGs. 6A-B
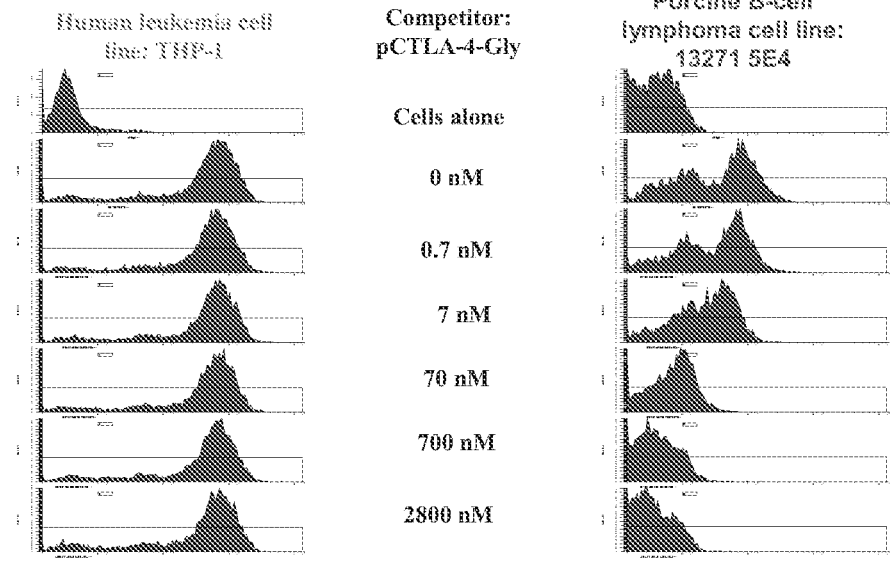
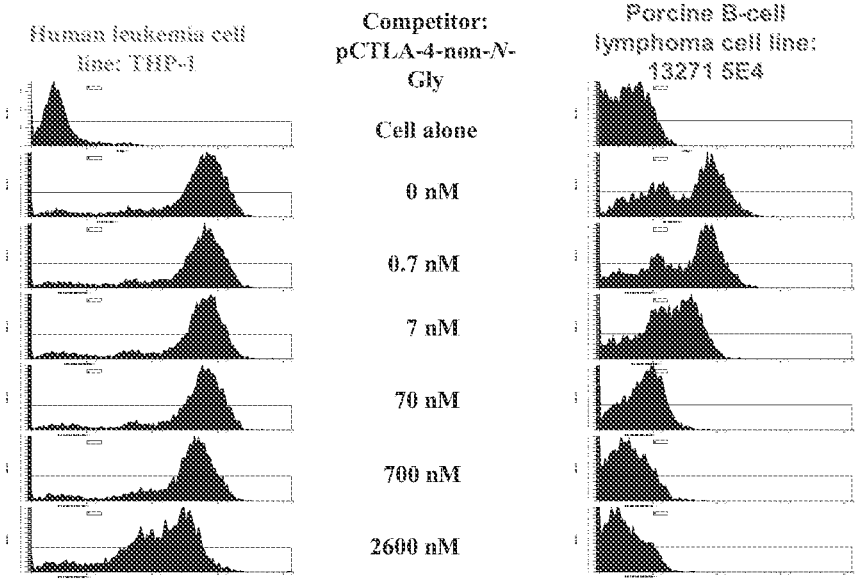

FIG. 8
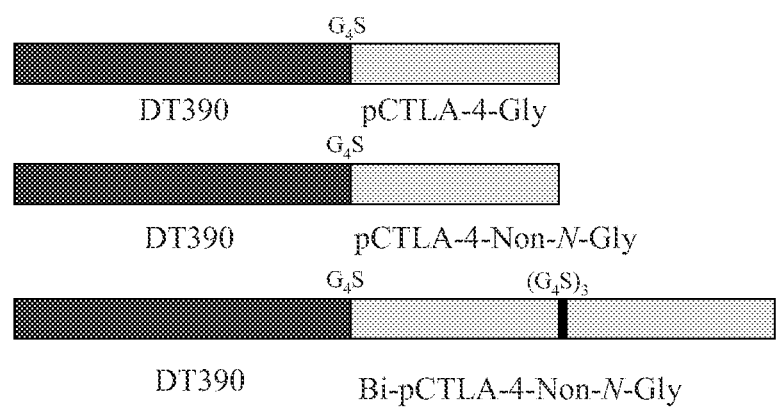
FIGs. 9A-B
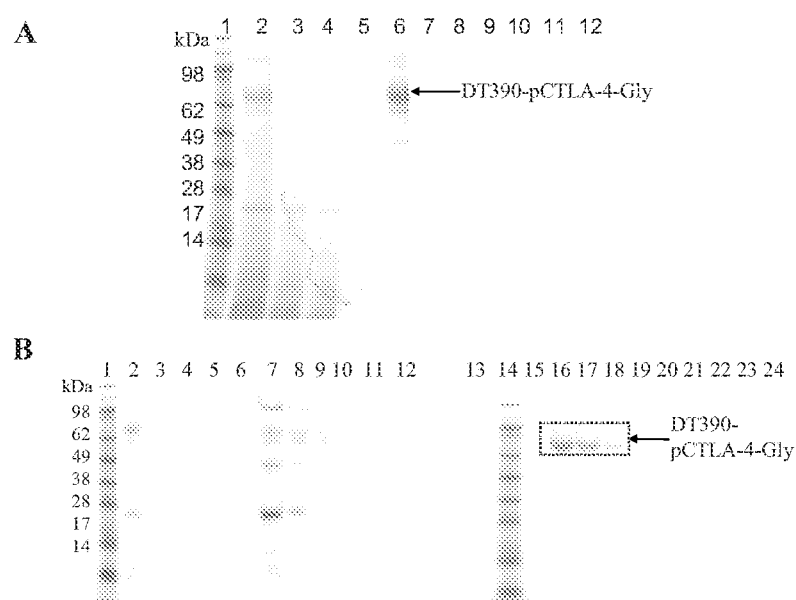

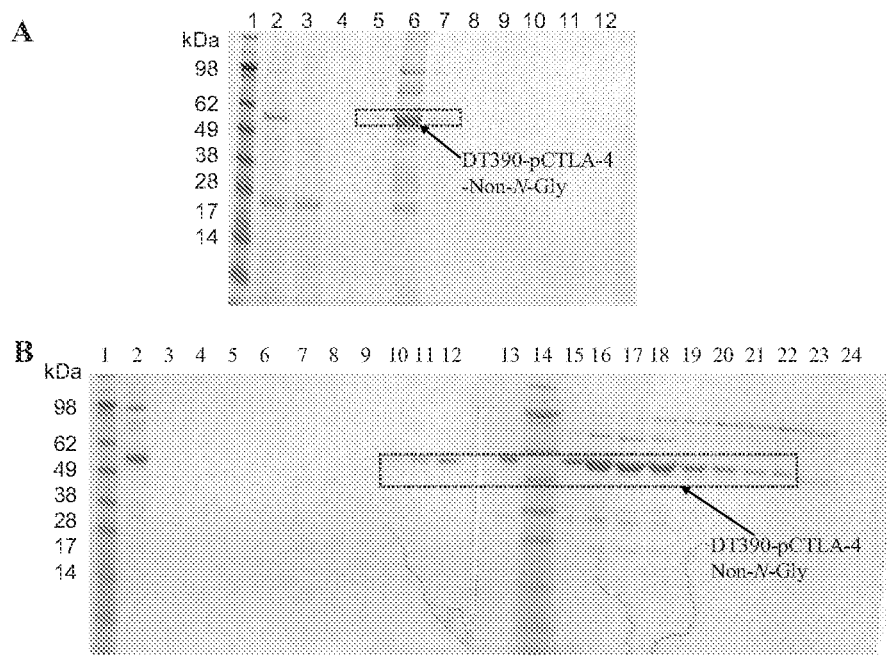
FIGs. 10A-B
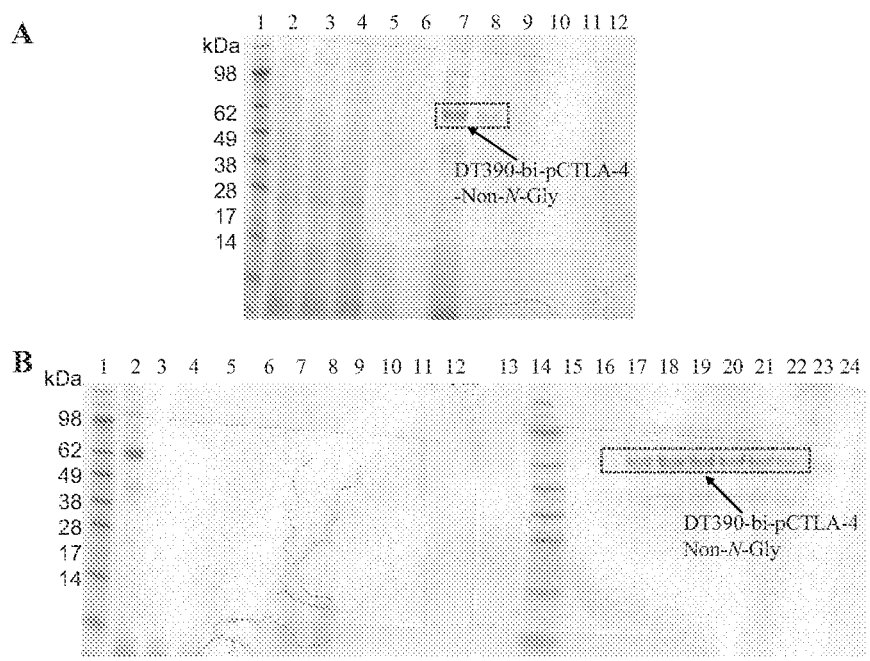
FIGs. 11A-B

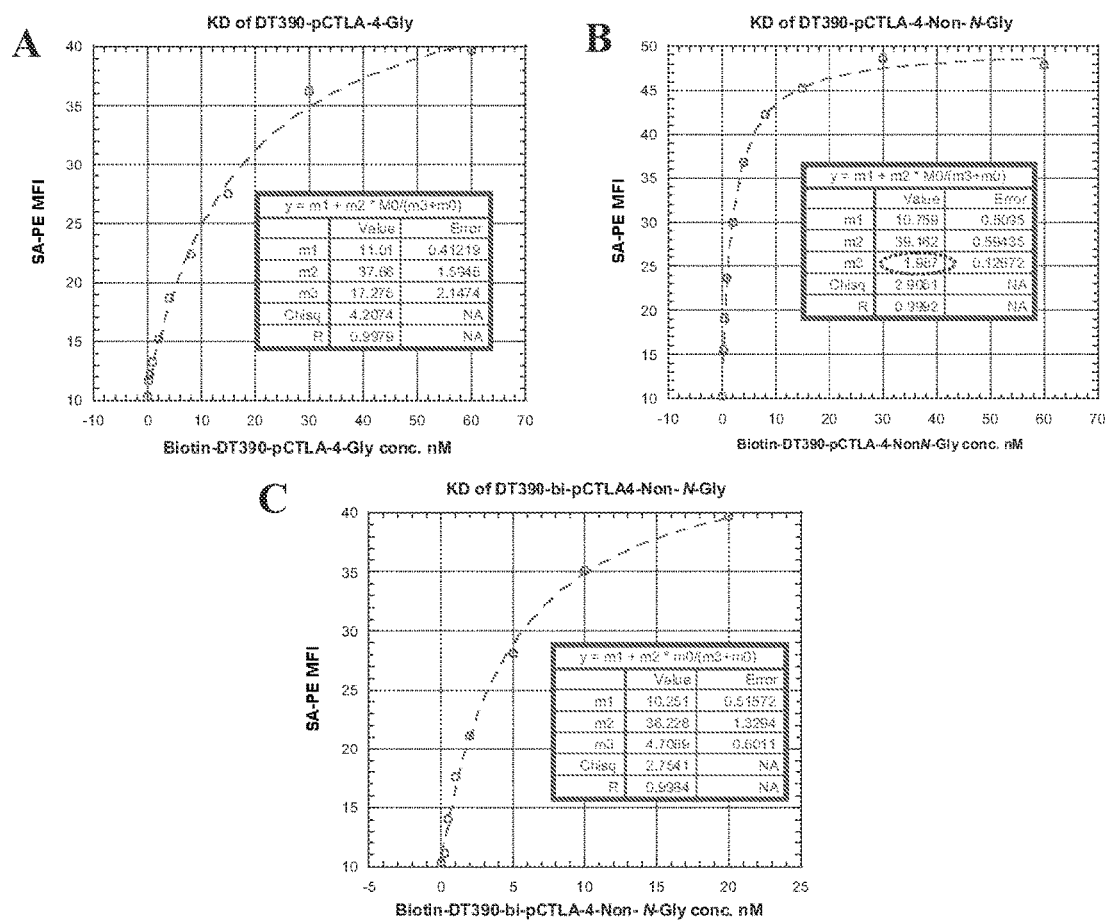
FIGs. 13A-C

FIG. 14

```
NonGly     AGADDVVDSSKSFVMENFASYHGTKPGYVDSIQKGIQKPKSGTQGNYDDDWKGFYSTDNK  60
Bi-NonGly  AGADDVVDSSKSFVMENFASYHGTKPGYVDSIQKGIQKPKSGTQGNYDDDWKGFYSTDNK  60
Gly        AGADDVVDSSKSFVMENFASYHGTKPGYVDSIQKGIQKPKSGTQGNYDDDWKGFYSTDNK  60
           ************************************************************

NonGly     YDAAGYSVDNENPLSGKAGGVVKVTYPGLTKVLALKVDNAETIKKELGLSLTEPLMEQVG  120
Bi-NonGly  YDAAGYSVDNENPLSGKAGGVVKVTYPGLTKVLALKVDNAETIKKELGLSLTEPLMEQVG  120
Gly        YDAAGYSVDNENPLSGKAGGVVKVTYPGLTKVLALKVDNAETIKKELGLSLTEPLMEQVG  120
           ************************************************************

NonGly     TEEFIKRFGDGASRVVLSLPFAEGSSSVEYINNWEQAKALSVELEINFETRGKRGQDAMY  180
Bi-NonGly  TEEFIKRFGDGASRVVLSLPFAEGSSSVEYINNWEQAKALSVELEINFETRGKRGQDAMY  180
Gly        TEEFIKRFGDGASRVVLSLPFAEGSSSVEYINNWEQAKALSVELEINFETRGKRGQDAMY  180
           ************************************************************

NonGly     EYMAQACAGNRVRRSVGSSLSCINLDWDVIRDKTKTKIESLKEHGPIKNKMSESPAKTVS  240
Bi-NonGly  EYMAQACAGNRVRRSVGSSLSCINLDWDVIRDKTKTKIESLKEHGPIKNKMSESPAKTVS  240
Gly        EYMAQACAGNRVRRSVGSSLSCINLDWDVIRDKTKTKIESLKEHGPIKNKMSESPAKTVS  240
           ************************************************************

NonGly     EEKAKQYLEEFHQTALEHPELSELKTVTGTNPVFAGANYAAWAVNVAQVIDSETADNLEK  300
Bi-NonGly  EEKAKQYLEEFHQTALEHPELSELKTVTGTNPVFAGANYAAWAVNVAQVIDSETADNLEK  300
Gly        EEKAKQYLEEFHQTALEHPELSELKTVTGTNPVFAGANYAAWAVNVAQVIDSETADNLEK  300
           ************************************************************

NonGly     TTAALSILPGIGSVMGIADGAVHHNTEEIVAQSIALSSLMVAQAIPLVGELVDIGFAAYN  360
Bi-NonGly  TTAALSILPGIGSVMGIADGAVHHNTEEIVAQSIALSSLMVAQAIPLVGELVDIGFAAYN  360
Gly        TTAALSILPGIGSVMGIADGAVHHNTEEIVAQSIALSSLMVAQAIPLVGELVDIGFAAYN  360
           ************************************************************

NonGly     FVESIINLFQVVHNSYNRPAYSPGHKTQPFLPWGGGGSMHVAQPAVVLANSRGVASFVCE  420
Bi-NonGly  FVESIINLFQVVHNSYNRPAYSPGHKTQPFLPWGGGGSMHVAQPAVVLANSRGVASFVCE  420
Gly        FVESIINLFQVVHNSYNRPAYSPGHKTQPFLPWGGGGSMHVAQPAVVLANSRGVASFVCE  420
           ************************************************************

NonGly     YGSAGKAAEVRVTVLRRAGSQMTEVCAATYTVEDELTFLDDSTCTGTSTENKVALTIQGL  480
Bi-NonGly  YGSAGKAAEVRVTVLRRAGSQMTEVCAATYTVEDELTFLDDSTCTGTSTENKVALTIQGL  480
Gly        YGSAGKAAEVRVTVLRRAGSQMTEVCAATYTVEDELTFLDDSTCTGTSTENKVNLTIQGL  480
           **************************************************** ******

NonGly     RAVDTGLYICKVELLYPPPYYVGMGAGTQIYVIDPEPCPDSDHHHHHH------------  528
Bi-NonGly  RAVDTGLYICKVELLYPPPYYVGMGAGTQIYVIDPEPCPDSDGGGGSGGGGSGGGGSMHV  540
Gly        RAVDTGLYICKVELLYPPPYYVGMGNGTQIYVIDPEPCPDSDHHHHHH------------  528
           ************************* *****************

NonGly     ------------------------------------------------------------
Bi-NonGly  AQPAVVLANSRGVASFVCEYGSAGKAAEVRVTVLRRAGSQMTEVCAATYTVEDELTFLDD  600
Gly        ------------------------------------------------------------

NonGly     ------------------------------------------------------------
Bi-NonGly  STCTGTSTENKVALTIQGLRAVDTGLYICKVELLYPPPYYVGMGAGTQIYVIDPEPCPDS  660
Gly        ------------------------------------------------------------

NonGly     --                                    SEQ ID NO:2
Bi-NonGly  DHHHHHH  667                          SEQ ID NO:3
Gly        --                                    SEQ ID NO:4
```

RECOMBINANT CYTOTOXIC T-LYMPHOCYTE-ASSOCIATED PROTEIN 4 (CTLA4)

CLAIM OF PRIORITY

This application is a U.S. National Phase Application under 35 U.S.C. §371 of International Patent Application No. PCT/US2013/028196, filed on Feb. 28, 2013, which claims the benefit of U.S. Provisional Application Ser. No. 61/617,345, filed on Mar. 29, 2012. The entire contents of the foregoing are hereby incorporated by reference herein.

FEDERALLY SPONSORED RESEARCH OR DEVELOPMENT

This invention was made with Government support under Grant Nos. 2P01AI45897, R00000000004609, and R00000000001796 awarded by the National Institutes of Health. The Government has certain rights in the invention.

TECHNICAL FIELD

This invention relates to recombinant CTLA-4 proteins, e.g., soluble CTLA-4 or recombinant CTLA-4 fusion toxins, and methods for making and using them.

BACKGROUND

T-cell proliferation and function depends on signals from the antigen-receptor complex (TCR/CD3) and by various co-stimulatory receptors such as CD28 and CTLA-4. The balance of positive and negative signals determines the outcome of the T-cell response of foreign and self-antigen. The most well studied co-stimulatory pairs are CD28/CTLA-4-CD80/CD86. CD28 is constitutively expressed on native and activated CD4 and CD8 positive T cells. CTLA-4 is expressed on activated T cells and plays a negative regulatory role in T cell response. CD80 and CD86 are induced on antigen presenting cells (APC) with their activation (Riha et al., 2010, Self Nonself. 1, 231-240; Sansom et al., 2000, Immunology, 101, 169-177). The discovery of co-stimulatory molecules introduced the possibility of therapeutic intervention at the level of the costimulatory signal without interference with an antigen-receptor (TCR/CD3) signal. One could dampen the co-receptor signal without needing to know the exact nature of the antigen involved in the antigen-receptor complex of T-cell activation cascade (Riha et al., 2010, Self Nonself. 1, 231-240). Therefore co-stimulation blockade has been broadly used to modulate the immune response for organ transplantation, autoimmune diseases as well as cancer treatment (Bour-Jordan et al., 2011, Immunol Rev. 241, 180-205). The higher affinity of CTLA-4 for CD80/CD86 has allowed the use of a CTLA-4-Ig fusion protein to out-compete CD28-CD80/CD86 binding in the treatment of autoimmune disorders (Riha et al., 2010, Self Nonself. 1, 231-240). It was also reported that the suppressive function of natural regulatory T cells is dependent on CTLA-4 (Sansom et al., 2000, Immunology, 101, 169-177; Wing et al., 2008, Science, 322, 271-275).

SUMMARY

At least in part, the present invention is based on the development of recombinant CTLA-4 proteins, e.g., soluble CTLA-4 or CTLA-4 fusion toxins, as well as non-N-glycosylated CTLA-4 proteins, e.g., that can be expressed in yeast, e.g., in *Pichia pastoris*. These recombinant proteins are useful for induction of organ transplantation tolerance, treatment of autoimmune disease and other conditions.

Thus in a first aspect the invention provides non-N-glycosylated human Cytotoxic T-Lymphocyte-Associated Protein 4 (CTLA4) proteins, e.g., soluble proteins, comprising or consisting of amino acids 39-152, e.g., 36-161, of SEQ ID NO:1, wherein
(i) the amino acid at position 113 is not Asparagine (N), and/or the amino and/or the amino acid at position 115 is neither Threonine (T) nor Serine (S); and
(ii) the amino acid at position 145 is not Asparagine (N), and/or the amino and/or the amino acid at position 147 is neither Threonine (T) nor Serine (S).

In some embodiments, the amino acids at positions 113 and 145 are Alanine (A) or Glycine (G). In some embodiments, the proteins further include mutations at L141 and/or A66, e.g., to L141E and/or A66Y.

In another aspect, the invention provides CTLA-4 fusion toxins comprising: a first part comprising or consisting of a cytotoxic protein, and a second part comprising a non-N-glycosylated human Cytotoxic T-Lymphocyte-Associated Protein 4 (CTLA4) comprising amino acids 39-152, e.g., 36-161, of SEQ ID NO:1, wherein
(i) the amino acid at position 113 is not Asparagine (N), and/or the amino and/or the amino acid at position 115 is neither Threonine (T) nor Serine (S); and
(ii) the amino acid at position 145 is not Asparagine (N), and/or the amino and/or the amino acid at position 147 is neither Threonine (T) nor Serine (S).

In some embodiments, the cytotoxic protein comprises diphtheria toxin, *Pseudomonas* exotoxin, or portions or variants thereof.

In some embodiments, the fusion toxins further include a third part comprising or consisting of a non-N-glycosylated human Cytotoxic T-Lymphocyte-Associated Protein 4 (CTLA4), e.g., comprising amino acids 39-152, e.g., 36-161, of SEQ ID NO:1, wherein
(i) the amino acid at position 113 is not Asparagine (N), and/or the amino and/or the amino acid at position 115 is neither Threonine (T) nor Serine (S); and
(ii) the amino acid at position 145 is not Asparagine (N), and/or the amino and/or the amino acid at position 147 is neither Threonine (T) nor Serine (S).

In some embodiments, the second or third part CTLA-4 proteins further include mutations at L141 and/or A66, e.g., to L141E and/or A66Y.

In some embodiments, the fusion toxins further include a linker between the first and second parts.

In another aspect, the invention provides codon-optimized nucleic acid molecules (e.g., optimized for expression in a methylotropic yeast, e.g., of the species *Pichia Pastoris*) encoding the non-N-glycosylated human CTLA-4 proteins described herein, e.g., the fusion toxins described herein, as well as vectors including the nucleic acid molecules, and host cells expressing the nucleic acid molecules. In some embodiments, the host cell is a methylotropic yeast, e.g., a cell of the species *Pichia Pastoris*.

In another aspect, the invention provides pharmaceutical compositions comprising the non-N-glycosylated human CTLA-4 proteins described herein, e.g., the fusion toxins described herein, and a physiologically acceptable carrier.

In another aspect, the invention provides methods for treating a subject who has an autoimmune disease, the method comprising administering to the subject a therapeutically effective amount of the fusion toxins described herein.

In yet another aspect, the invention provides methods for inducing tolerance in a subject who has undergone or will undergo an organ transplantation procedure, the method comprising administering to the subject a therapeutically effective amount of the fusion toxins described herein.

Also provided herein are CTLA-4 proteins, e.g., fusion toxins, described herein for treating an autoimmune disease or inducing tolerance to a transplanted organ, and the use of the CTLA-4 proteins, e.g., fusion toxins, described herein in the manufacture of a medicament for treating an autoimmune disease or inducing tolerance to a transplanted organ.

In another aspect, the invention provides methods for producing a non-N-glycosylated human CTLA-4. The methods include expressing a non-N-glycosylated human CTLA-4 comprising amino acids 39-152, e.g., 36-161, of SEQ ID NO:1, wherein
(i) the amino acid at position 113 is not Asparagine (N), and/or the amino and/or the amino acid at position 115 is neither Threonine (T) nor Serine (S); and
(ii) the amino acid at position 145 is not Asparagine (N), and/or the amino and/or the amino acid at position 147 is neither Threonine (T) nor Serine (S),
in a methylotropic yeast; and substantially purifying the non-N-glycosylated human CTLA-4, thereby producing the composition. In some embodiments, the CTLA-4 proteins further include mutations at L141 and/or A66, e.g., to L141E and/or A66Y. In some embodiments, the methods are used to produce a fusion toxin as described herein.

In some embodiments, the methylotropic yeast is of the species *Pichia Pastoris*.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Construction of the glycosylated or non-N-glycosylated soluble porcine CTLA4-6×His (pCTLA4-6×His) into pwPICZalpha between XhoI and EcoRI sites. pwPICZalpha was derived from the pPICZalpha vector (Invitrogen). pwPICZalpha contains a unique XhoI site and the original BamHI and NcoI sites were removed by mutation. AOX1: AOX1 region; AOX1 TT: AOX1 transcription termination region; TEF1: TEF1 promoter region; EM7: EM7 promoter region; Zeocin: Zeocin resistance gene (Sh ble ORF); CYC1: CYC1 transcription termination region; ColE1: ColE1 origin (pUC-derived).

FIGS. 2A-B. Purification for glycosylated soluble porcine CTLA-4: A) First step purification using Ni-Sepharose 6 fast flow resin. Lane 1 and 14: protein markers; Lane 2: sample; Lane 3: flowthrough; Lane 4: washing; Lane 5-12: eight 50 mL elution fractions using 100 mM imidazole; Lane 13 and 15-21: eight 50 mL elution fractions using 200 mM imidazole. B) Second step purification using strong anion-exchange resin Poros 50HQ. Lane 1 and 14: protein markers; Lane 2: sample; Lane 3: flowthrough; Lane 4-5: two 40 mL washing fractions; Lane 6-13: eight 10 mL elution fractions using 100 mM sodium borate; Lane 15-22: eight 10 mL elution fractions using 200 mM sodium borate; Lane 23-24: flushing using 1 M NaCl.

FIGS. 3A-B. N-linked glycosylation analysis for soluble porcine CTLA-4 using PNGase F. A) 12% NuPAGE SDS gel analysis. B) Western blot analysis using mouse anti-His mAb (1.1 μg/mL, Invitrogen) and HRP-rat anti-mouse IgG (1.25 μg/mL, Invitrogen). Lane 1: protein marker; Lane 2: with PNGase F enzyme to remove N-linked glycosylation; Lane 3: without PNGase F enzyme. Soluble porcine CTLA-4 is approximately 14.1 kDa.

FIGS. 4A-C. Purification for non-N-glycosylated soluble porcine CTLA-4: A) First step purification using Ni-Sepharose 6 fast flow resin. Lane 1 and 14: protein markers; Lane 2: sample; Lane 3: flowthrough; Lane 4: washing; Lane 5-12: eight 50 mL elution fractions using 100 mM imidazole; Lane 13 and 15-21: eight 50 mL elution fractions using 200 mM imidazole. B) Second step purification using strong anion-exchange resin Poros 50HQ. Lane 1 and 14: protein markers; Lane 2: sample; Lane 3: flowthrough; Lane 4-5: two 40 mL washing fractions; Lane 6-13: eight 10 mL elution fractions using 100 mM sodium borate; Lane 15-22: eight 10 mL elution fractions using 200 mM sodium borate. Lane 23: flushing using 1 M NaCl. C) 12% NuPAGE SDS gel analysis for the final product of non-N-glycosylated soluble porcine CTLA-4 (14.1 kDa). The weak band seen at approximately 28 kDa is a covalent homodimer of the non-N-glycosylated soluble porcine CTLA-4 generated by disulfide bond formation (analyzed under reduced conditions using DTT and beta-mercaptoethanol).

FIGS. 5A-B. FACS binding analysis for biotinylated A) glycosylated or B) non-N-glycosylated soluble porcine CTLA-4 using porcine CD80-expressing B-cell lymphoma cell line (LCL13271-5E4) shown in the column on the right. Human CD80-expressing leukemia cell line THP-1 was included as positive control cell line for the hamster anti-mouse CD80 mAb (clone 16-10A1) shown in the column on the left.

FIGS. 6A-B. Blocking/competition analysis for the binding of hamster anti-mouse CD80 mAb (clone 16-10A1) to the porcine CD-80 expressing B-cell lymphoma cell line (LCL13271-5E4), shown in the column on the right, using non-biotinylated A) glycosylated or B) non-N-glycosylated porcine soluble CTLA-4. Human CD80-expressing leukemia cell line THP-1, shown in the column on the left, was included as positive control cell line for the hamster anti-mouse CD80 mAb clone 16-10A1. Concentrations listed represent the concentration of the non-biotinylated soluble porcine CTLA-4 competitor. The concentration of the biotinylated hamster anti-mouse CD80 mAb is 17 nM.

FIGS. 7A-B. $K_D$ determination using flow cytometry and nonlinear least squares fit. MFI was plotted over a wide range concentration of biotinylated A) glycosylated or B) non-N-glycosalated soluble porcine CTLA-4. The accompanying least-squares fits and the parameters are shown based on the hyperbolic equation $y=m1+m2*m0/(m3+m0)$ where y=MFI at the given biotinylated soluble porcine CTLA-4 concentration, m0=biotinylated soluble porcine CTLA-4 concentration, m1=MFI of zero biotinylated soluble porcine CTLA-4 control, m2=MFI at saturation and $m3=K_D$. The inset table in A) showed a fitted $K_D$ of 13 nM for glycosalated soluble porcine CTLA-4. The inset table in B) showed a fitted $K_D$ of 13 nM for non-N-glycosalated soluble porcine CTLA-4.

FIG. 8. Schematic presentation of the three versions of porcine CTLA-4 fusion toxin.

FIGS. 9A-B. Purification of glycosylated soluble porcine CTLA-4 fusion toxin DT390-pCTLA-4-Gly: A) First step purification using Ni-Sepharose 6 fast flow resin. Lane 1: protein marker; Lane 2: sample; Lane 3: flowthrough; Lane 4: washing; Lane 5-12: eight 50 mL elution fractions using 500 mM imidazole. B) Second step purification using strong anion-exchange resin Poros 50HQ. Lane 1 and 14: protein markers; Lane 2: sample; Lane 3: flowthrough; Lane 4-5: two 40 mL washing fractions; Lane 6-13: eight 10 mL elution fractions using 200 mM sodium borate; Lane 15-22: eight 10 mL elution fractions using 200 mM sodium borate+ 50 mM NaCl; Lane 23-24: flushing using 1 M NaCl.

FIGS. 10A-B. Purification for non-N-glycosylated soluble porcine CTLA-4 fusion toxin DT390-pCTLA-4-Non-N-Gly: A) First step purification using Ni-Sepharose 6 fast flow resin. Lane 1: protein marker; Lane 2: sample; Lane 3: flowthrough; Lane 4: washing; Lane 5-12: eight 50 mL elution fractions using 500 mM imidazole. B) Second step purification using strong anion-exchange resin Poros 50HQ. Lane 1 and 14: protein markers; Lane 2: sample; Lane 3: flowthrough; Lane 4-5: two 40 mL washing fractions; Lane 6-13: eight 10 mL elution fractions using 200 mM sodium borate; Lane 15-22: eight 10 mL elution fractions using 200 mM sodium borate+50 mM NaCl; Lane 23-24: flushing using 1 M NaCl.

FIGS. 11A-B. Purification for bi-non-N-glycosylated soluble porcine CTLA-4 fusion toxin DT390-pCTLA-4-bi-Non-N-Gly: A) First step purification using Ni-Sepharose 6 fast flow resin. Lane 1: protein marker; Lane 2: sample; Lane 3-4: flowthrough; Lane 5: washing; Lane 6-12: seven 50 mL elution fractions using 500 mM imidazole. B) Second step purification using strong anion-exchange resin Poros 50HQ. Lane 1 and 14: protein markers; Lane 2: sample; Lane 3: flowthrough; Lane 4-5: two 40 mL washing fractions; Lane 6-13: eight 10 mL elution fractions using 200 mM sodium borate; Lane 15-22: eight 10 mL elution fractions using 200 mM sodium borate+50 mM NaCl; Lane 23-24: flushing using 1 M NaCl.

Figure 12:
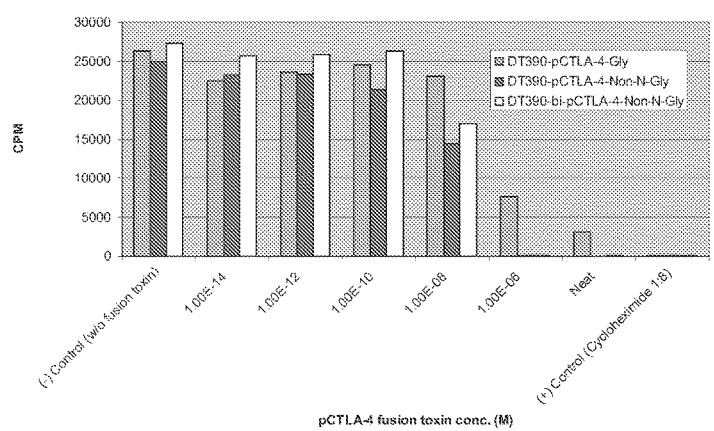

FIG. 12. In vitro protein synthesis inhibition assay using a porcine CD80-expressing B-cell lymphoma cell line LCL13271-5E4 for three versions of the porcine CTLA-4 fusion toxins: 1) DT390-pCTLA-4-Gly (blue bars, neat concentration: 2.63E-6 M); 2) DT390-pCTLA-4-Non-N-Gly (red bars, neat concentration: 4.38E-6 M); and 3) DT390-bi-pCTLA-4-Non-N-Gly (pale yellow bars, neat concentration: 1.55E-6M). Y-axis: cpm value by incorporating the tritium-labeled leucine. X-axis: plated porcine CTLA-4 fusion toxin concentration. Cyclohexmide is positive control.

FIGS. 13A-C. KD determination using flow cytometry and nonlinear least squares fit. MFI was plotted over a wide range concentration of biotinylated A) DT390-pCTLA-4-Gly, or B) DT390-pCTLA-4-Non-N-Gly, or C) DT390-bi-pCTLA4-Non-N-Gly. The accompanying least-squares fits and the parameters are shown based on the hyperbolic equation y=m1+m2*m0/(m3+m0) where y=MFI at the given biotinylated porcine CTLA-4 fusion toxin concentration, m0=biotinylated porcine CTLA-4 fusion toxin concentration, m1=MFI of zero biotinylated porcine CTLA-4 fusion toxin control, m2=MFI at saturation and m3=KD. The inset table in A) showed a fitted KD of 17.3 nM for DT390-pCTLA-4-Gly. The inset table in B) showed a fitted KD of 2 nM for DT390-pCTLA-4-Non-N-Gly. The inset table in C) showed a fitted KD of 4.7 nM for DT390-pCTLA-4-bi-Non-N-Gly.

FIG. 14. Comparison of the amino acid sequence of three versions of porcine DT390-pCTLA-4 fusion toxin.

DETAILED DESCRIPTION

Co-stimulation blockade can be used to modulate the immune response for induction of organ transplantation tolerance, treatment of autoimmune disease as well as cancer treatment. Cytotoxic T-Lymphocyte Antigen-4 (CTLA-4), also known as CD152, is an important co-stimulatory molecule which serves as a negative regulator for T cell proliferation and differentiation. CTLA-4/CD28-CD80/CD86 pathway is a critical co-stimulatory pathway for adaptive immune response. T cell activation through the T cell receptor and CD28 leads to increased expression of CTLA-4, an inhibitory receptor for CD80 and CD86.

As demonstrated herein, both glycosylated and non-N-glycosylated soluble porcine CTLA-4 could bind to porcine CD80-expressing B-cell lymphoma cell line directly and competitively inhibit the binding of an anti-CD80 monoclonal antibody to porcine CD80-expressing B-cell lymphoma cell line (See, e.g., Examples 1-3). This data demonstrated that there is no binding difference for the glycosylated and non-N-glycosylated porcine CTLA-4 to CD80-expressing B-cell lymphoma cell line. However, non-N-glycosylated soluble porcine CTLA-4 fusion toxin was more fully functional in inhibiting protein synthesis in target cells. Inhibition of protein synthesis requires the internalization of the fusion toxin. The high-mannose N-glycolylation of the yeast *Pichia pastoris* may not only have influenced the conformation for the binding but also hindered the internalization of the fusion toxin; removal of the N-glycosylation sites is one approach to be sure that fusion toxins expressed in *Pichia pastoris* are fully functional.

Described herein are the successful development of porcine CTLA-4 and a functional CTLA-4 fusion toxin, DT390-pCTLA-4-Non-N-Gly. The CTLA-4 fusion toxin can be used, e.g., to treat autoimmune diseases and induce tolerance on organ transplantation, as well as for cancer treatment, e.g., for cancers associated with malignant cells that express CD80 and/or CD86.

Non-Glycosylated Porcine CTLA-4

It has been reported that CTLA-4 binds to CD80/CD86 using the conserved signature binding motif "MYPPPY" for mammalian species (Bour-Jordan et al., 2011, Immunol Rev. 241, 180-205), however for pig "LYPPPY" is used (Vaughan et al., 2000, J Immunol. 165, 3175-3181). This study demonstrated that soluble porcine CTLA-4 cannot bind to human CD80-expressing leukemia cell line THP-1. This provides additional direct evidence for the importance of the methionine to leucine substitution at the signature motif to abolish the binding of porcine CTLA-4 to human CD80 as reported by Vaughan et al., 2000 (J Immunol. 165, 3175-3181). This soluble porcine CTLA-4 could be used in pig to human or non-human primate transplantation to specifically inhibit the donor APC-costimulated T cell response. As expected, the mutation of the N-linked glycosylation sites did not influence the binding of the non-N-glycosylated porcine soluble CTLA-4 to CD80-expressing porcine B-cell lymphoma cell line LCL13271-5E4.

Increased expression of CD80 on podocytes has been identified as a likely cause of proteinuria in minimal change disease (Garin et al., 2010, Kidney Int. 78, 296-302). CTLA-4 appears to regulate CD80 expression in podocytes, and to be altered in minimal change disease patients. The availability of soluble porcine CTLA-4 allows new treatment regimens for proteinuria, e.g., associated with pig-primate (e.g., human) renal transplantation (Yamada et al., 2005, Nat. Med. 11, 32-34).

CTLA-4 Fusion Toxins

The truncated diphtheria toxin DT390 has been successfully used to build recombinant immunotoxins (Woo et al 2002, Kim et al 2007, and Wang et al 2011). The antibody moiety was placed C-terminal to DT390 to prevent any interference with the translocation of biologically active diphtheria toxin A chain. In this study full use was made of the natural high-binding affinity advantage between CTLA-4 and CD80/CD86 and fused glycosylated or non-N-glycosylated soluble porcine CTLA-4 onto the truncated diphtheria toxin DT390 yielding porcine CTLA-fusion toxins. The target cell depletion function was assessed using protein synthesis inhibition assay and the specific binding affinity to the target cell was analyzed using flow cytometry.

The FDA-approved recombinant protein drug, human CTLA4-Ig (abatacept or belatacept, which differs from abatacept by including 2 amino acid substitutions, L141E and A66Y, numbered as in SEQ ID NO:1, below; both comprise an Fc fragment of a human IgG1 immunoglobulin linked to the extracellular domain of CTLA-4; Larsen et al., 2005, Am J Transplant, 5:443-53), binds to human CD80- or CD86-expressing APC, but does not significantly deplete their numbers. The CTLA-4 fusion toxins described herein can both bind to and deplete the CD80- or CD86-expressing porcine APC through protein synthesis inhibition. Porcine APC depletion function is a highlight of this reagent.

Cytotoxic T-Lymphocyte-Associated Protein 4 (CTLA4)

The proteins described herein comprise a CTLA-4 sequence. A number of CTLA-4 sequences are known in the art and can be used in the constructs described herein. For example, all or part of the soluble human CTLA-4 sequence can be used, e.g., as set forth at GenBank Acc. Nos. NM_001037631.2 (nucleic acid) and NP_001032720.1 (amino acid); that amino acid sequence is as follows:

```
                                         (SEQ ID NO: 1)
  1   maclgfqrhk aqlnlatrtw pctllfflll ipvfckamhv
      aqpavvlass rqiasfvcey 61   aspgkatevr vtvlrqadsq vtevcaatym mgneltfldd
      sictgtssgn qvNltiqglr 121   amdtglyick velmypppyy lgigNgtqiy viakekkpsy
      nrglcenapn rarm
```

N-linked glycosylation sites (N113 and N145) are shown in upper case. In some embodiments, only the extracellular domain, e.g., amino acids 39-152, e.g., 36-161, of SEQ ID NO:1 are used. Additional sequences of CTLA-4, e.g., from other species, are known in the art; porcine CTLA-4 is described herein, and others are as follows; in general, portions of the sequences that do not include any transmembrane regions are used (such regions can be identified using methods known in the art, including by reference to the GenBank database, or hydrophobicity plotting):

| | | |
|---|---|---|
| *H. sapiens* | NP_005205.2 | 223 aa |
| *P. troglodytes* | XP_526000.1 | 223 aa |
| *C. lupus* | NP_001003106.1 | 223 aa |
| *B. taurus* | NP_776722.1 | 221 aa |
| *M. musculus* | NP_033973.2 | 223 aa |
| *R. norvegicus* | NP_113862.1 | 223 aa |
| *G. gallus* | NP_001035180.1 | 205 aa |
| *F. catus* | NP_001009236.1 | 223 aa |

-continued

| | | |
|---|---|---|
| *S. scrofa* | NP_999314.1 | 223 aa |
| *O. aries* | NP_001009214.1 | 221 aa |

In some embodiments, a CTLA-4 sequence from another species will be used, e.g., wherein the subject to be treated, or organ donor in the case of transplantation, is of another species.

Where less than all of SEQ ID NO:1 is used, the fragment must retain the ability to bind CD80 and/or CD86.

In some embodiments, a CTLA-4 sequence lacking the signal sequence, e.g., lacking a sequence corresponding to amino acids 1-35, 1-36, 1-27, 1-38, or 1-39 of SEQ ID NO:1 is used. In some embodiments, a CTLA-4 sequence lacking the transmembrane domain, e.g., lacking amino acids corresponding to amino acids 153-174, or 163-174, of SEQ ID NO:1 is used. In some embodiments, a sequence lacking both a signal sequence and a transmembrane domain is used. In some embodiments, a sequence corresponding to amino acids 36-174 of SEQ ID NO:1 are used; in some embodiments, a sequence corresponding to amino acids 39-152 of SEQ ID NO:1 are used; in some embodiments, the CTLA-4 sequence used comprises a fragment comprising a sequence corresponding to amino acids 134-139 of SEQ ID NO:1 that retains the ability to bind CD80 or CD86, and optionally a sequence corresponding to amino acids 58-131 (the IGv domain); and/or a sequence corresponding to amino acids 39-152 (the IgV_CTLA-4 domain). In some embodiments, a sequence as set forth in U.S. Pat. Nos. 5,851,795; 5,434,131; 5,885,579; 5,844,095; 5,968,510; 5,977,318; 5,885,796, or Larsen et al., 2005, Am J Transplant, 5:443-53, or fragment thereof lacking a signal sequence and/or transmembrane domain, is used.

In some embodiments, the methods include altering the CTLA-4 sequence to remove N-linked glycosylation sites. The consensus sequence for N-linked glycosylation is Asn-Xaa-[Ser/Thr]; disruption can be achieved by mutation of the Asn, or the Ser/Thr. Referring to SEQ ID NO:1, above, there are N-linked glycosylation consensus sites at N113 and N145; disruption of these sites can be achieved by mutating N113 or T115, and N145 or T146. A mutation at N113 or N145 can be to any amino acid other than N, and a mutation at T115 or T146 can be to any amino acid other than T or S, so long as the mutation substantially preserves the CD80/CD86 binding ability, i.e., the mutant retains at least 20% of the affinity of the wild type molecule, e.g., at least 30%, 40%, 50%, 60%, 70%, 80%, 90%, 95%, or more of the function of the wild type molecule, e.g., in an in vitro assay as known in the art or described herein. In some embodiments, the mutations include N113A and N145A.

In some embodiments, the mutation is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III of US20110201052; pages 13-15 "Biochemistry" 2$^{nd}$ ED. Stryer ed (Stanford University); Henikoff et al., PNAS 1992 Vol 89 10915-10919; Lei et al., J Biol Chem May 19, 1995; 270(20):11882-6). In some embodiments, the protein includes a mutation at N113 and/or N145 to alanine or glycine. In some embodiments, the protein includes a mutation at N113 and/or N145 to a glutamine. In some embodiments, the protein includes a mutation at N113 and/or N145 to an aspartate or glutamate.

In some embodiments, instead of or in addition to a mutation at N113 or N145, the mutant includes a mutation at T115 and/or T146 to any amino acid other than serine or threonine, thereby disrupting the N-linked glycosylation consensus site. In some embodiments, the mutation at T115 and/or T146 is to alanine or glycine.

In some embodiments, the methods include introducing one or more additional mutations into the CTLA-4 sequence, e.g., L141E and/or A66Y (numbered with regard to SEQ ID NO:1) as described in Larsen et al., 2005, Am J Transplant, 5:443-53. Thus, in some embodiments, the sequence can be at least 80%, 85%, 90%, 95%, or 99% identical to at least 60%, 70%, 80%, 90%, or 100% of a soluble CTLA-4 sequence, e.g., SEQ ID NO:1; e.g., the sequence can include 1, 2, 3, 4, 5, 6, 7, 8, 9, 10, 11, 12, 13, 14, 15, 16, 17, 18, 19, or 20 mutations.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is typically at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Fusion Proteins

In some embodiments, the recombinant CTLA-4 proteins described herein are fusion proteins, and include a non-CTLA-4 sequence fused to the N or C terminal of the CTLA-4. In some embodiments, the non-CTLA-4 sequence is a cytotoxic protein, e.g., Idarubicin; CRM9 (e.g., FN18-CRM9, Knechtle et al., Transplantation 1997; 63:1-6); or pokeweed antiviral protein. In some embodiments, the cytotoxic protein is a bacterial toxin, e.g., diphtheria toxin (DT) or portions or variants thereof, e.g., as described in Aullo et al., EMBO J. 11(2):575-83 (1992); Abi-Habib et al., Blood. 104(7):2143-2148 (2004); Perentesis et al., Proc. Natl. Acad. Sci. USA 85:8386-8390 (1988); Zettlemeissl et al., Gene. 41(1):103-111 (1986); US 2009/0010966; US20090041797; U.S. Pat. No. 5,843,711; U.S. Pat. No. 7,585,942; U.S. Pat. No. 7,696,338; US20080166375; or *Pseudomonas* exotoxin (PE), or portions or variants thereof, e.g., as described in U.S. Pat. Nos. 4,545,985; 4,892,827; 5,458,878; 7,314,632; Song et al., Protein Expression and Purification 44(1):52-57 (2005); Theuer et al., J. Biol. Chem. 267(24):16872-16877 (1992); Heimbrook et al., Proc Natl Acad Sci USA. 87(12): 4697-4701 (1990); Debinski et al., Mol Cell Biol. 11(3): 1751-1753 (1991); Chaudhary et al., Proc. Nadl. Acad. Sci. USA 87:308-312 (1990). In some embodiments, the cytotoxic protein is a plant toxin, e.g., a plant holotoxin (e.g., class II ribosome-inactivating proteins such as ricin (e.g., deglycosylated ricin A chain (dgA)), abrin, mistletoe lectin, or modeccin) or hemitoxin (class I ribosome-inactivating proteins, e.g., PAP, saporin, bryodin 1, bouganin, or gelonin), or fragments or variants thereof that retain cytotoxic activity. See, e.g., Neville et al., J Contr Rel 1993; 24:133-141; Vallera, Blood 1994; 83:309-317; Vitetta et al., Immunology Today 1993; 14:252-259; Kreitman et al., AAPS Journal. 2006; 8(3):E532-E551). Suitable sequences are known in the art.

Peptide Tags

In some embodiments, the proteins or fusion proteins further include a peptide tag useful for purification. In some embodiments, the tag comprises histidines, e.g., two or more, e.g., three, four, five or six histidine residues at the C-terminus (i.e., as shown at positions 662-667 of SEQ ID NO:3, FIG. 14), and purification is achieved by binding to a nickel or cobalt column. In some embodiments, the tag comprises glutathione-S-transferase (GST) and recovery is by affinity to substrate glutathione bound to a column, e.g. glutathione sepharose. In some embodiments, the tag comprises a FLAG peptide (e.g., N-DYKDDDDK-C (SEQ ID NO:5) or a variant thereof) and protein is recovered with specific antibody to the peptide. In some embodiments, the tag comprises an epitope derived from the Influenza protein haemagglutinin (HA) (e.g., N-YPYDVP-C (SEQ ID NO:6)) and protein is recovered using an anti-HA antibody that binds the epitope. In some embodiments, the tag comprises an epitope derived from the human proto-oncoprotein myc (e.g., N-ILKKATAYIL-C (SEQ ID NO:7), or N-EQKLI-SEEDL-C (SEQ ID NO:8)), and recovery is performed with an anti-myc antibody.

In some embodiments, the protein further comprises a proteolytic cleavage site between the purification tag and the CTLA-4 sequence, and after purification the protein is treated with the protease to remove the purification tag. Examples include the PreScission protease, thrombin, and factor Xa. Enterokinase sites that enable tag cleavage without leaving behind extra amino acids are preferred. In some embodiments, an exopeptidase is used to remove N-terminal His-tags (e.g., Qiagen TAGZyme). See, e.g., *The Recombinant Protein Handbook, Protein Amplification and Simple*

*Purification*, Amersham Biosciences, available online at 130.15.90.245/methods/handbooks %20 and %20 manuals/the%20recombinant%20protein%20handbook.pdf.

Codon Optimization

In addition, the nucleic acid sequences used in the present methods are preferably codon-optimized for expression in a selected expression system, e.g., in *Pichia pastoris* (See, e.g., Woo et al., 2002). In order to optimize expression in non-mammalian cells, codon optimization specific for a selected host organism can be used. For example, in embodiments where *P. pastoris* is used as a host organism, the following Table 1 (source: kazusa.or.jp) can be used to select codons:

TABLE 1

Codon Optimization Table for *Pichia Pastoris*

| triplet | UUU | UCU | UAU | UGU |
|---|---|---|---|---|
| amino acid | F | S | Y | C |
| fraction | 0.54 | 0.29 | 0.47 | 0.64 |
| frequency: per 1000 | 24.1 | 24.4 | 16.0 | 7.7 |
| (number) | (1963) | (1983) | (1300) | (626) |
| triplet | UUC | UCC | UAC | UGC |
| amino acid | F | S | Y | C |
| fraction | 0.46 | 0.20 | 0.53 | 0.36 |
| frequency: per 1000 | 20.6 | 16.5 | 18.1 | 4.4 |
| (number) | (1675) | (1344) | (1473) | (356) |
| triplet | UUA | UCA | UAA | UGA |
| amino acid | L | S | * | * |
| fraction | 0.16 | 0.18 | 0.51 | 0.20 |
| frequency: per 1000 | 15.6 | 15.2 | 0.8 | 0.3 |
| (number) | (1265) | (1234) | (69) | (27) |
| triplet | UUG | UCG | UAG | UGG |
| amino acid | L | S | * | W |
| fraction | 0.33 | 0.09 | 0.29 | 1.00 |
| frequency: per 1000 | 31.5 | 7.4 | 0.5 | 10.3 |
| (number) | (2562) | (598) | (40) | (834) |
| triplet | CUU | CCU | CAU | CGU |
| amino acid | L | P | H | R |
| fraction | 0.16 | 0.35 | 0.57 | 0.17 |
| frequency: per 1000 | 15.9 | 15.8 | 11.8 | 6.9 |
| (number) | (1289) | (1282) | (960) | (564) |
| triplet | CUC | CCC | CAC | CGC |
| amino acid | L | P | H | R |
| fraction | 0.08 | 0.15 | 0.43 | 0.05 |
| frequency: per 1000 | 7.6 | 6.8 | 9.1 | 2.2 |
| (number) | (620) | (553) | (737) | (175) |
| triplet | CUA | CCA | CAA | CGA |
| amino acid | L | P | Q | R |
| fraction | 0.11 | 0.42 | 0.61 | 0.10 |
| frequency: per 1000 | 10.7 | 18.9 | 25.4 | 4.2 |
| (number) | (873) | (1540) | (2069) | (340) |
| triplet | CUG | CCG | CAG | CGG |
| amino acid | L | P | Q | R |
| fraction | 0.16 | 0.09 | 0.39 | 0.05 |
| frequency: per 1000 | 14.9 | 3.9 | 16.3 | 1.9 |
| (number) | (1215) | (320) | (1323) | (158) |
| triplet | AUU | ACU | AAU | AGU |
| amino acid | I | T | N | S |
| fraction | 0.50 | 0.40 | 0.48 | 0.15 |
| frequency: per 1000 | 31.1 | 22.4 | 25.1 | 12.5 |
| (number) | (2532) | (1820) | (2038) | (1020) |
| triplet | AUC | ACC | AAC | AGC |
| amino acid | I | T | N | S |
| fraction | 0.31 | 0.26 | 0.52 | 0.09 |
| frequency: per 1000 | 19.4 | 14.5 | 26.7 | 7.6 |
| (number) | (1580) | (1175) | (2168) | (621) |
| triplet | AUA | ACA | AAA | AGA |
| amino acid | I | T | K | R |
| fraction | 0.18 | 0.24 | 0.47 | 0.48 |
| frequency: per 1000 | 11.1 | 13.8 | 29.9 | 20.1 |
| (number) | (906) | (1118) | (2433) | (1634) |
| triplet | AUG | ACG | AAG | AGG |
| amino acid | M | T | K | R |
| fraction | 1.00 | 0.11 | 0.53 | 0.16 |
| frequency: per 1000 | 18.7 | 6.0 | 33.8 | 6.6 |
| (number) | (1517) | (491) | (2748) | (539) |
| triplet | GUU | GCU | GAU | GGU |
| amino acid | V | A | D | G |
| fraction | 0.42 | 0.45 | 0.58 | 0.44 |
| frequency: per 1000 | 26.9 | 28.9 | 35.7 | 25.5 |
| (number) | (2188) | (2351) | (2899) | (2075) |
| triplet | GUC | GCC | GAC | GGC |
| amino acid | V | A | D | G |
| fraction | 0.23 | 0.26 | 0.42 | 0.14 |
| frequency: per 1000 | 14.9 | 16.6 | 25.9 | 8.1 |
| (number) | (1210) | (1348) | (2103) | (655) |
| triplet | GUA | GCA | GAA | GGA |
| amino acid | V | A | E | G |
| fraction | 0.15 | 0.23 | 0.56 | 0.33 |
| frequency: per 1000 | 9.9 | 15.1 | 37.4 | 19.1 |
| (number) | (804) | (1228) | (3043) | (1550) |
| triplet | GUG | GCG | GAG | GGG |
| amino acid | V | A | E | G |
| fraction | 0.19 | 0.06 | 0.44 | 0.10 |
| frequency: per 1000 | 12.3 | 3.9 | 29.0 | 5.8 |
| (number) | (998) | (314) | (2360) | (468) |

Protein Production Methods

The methods for producing non-N-glycosylated human CTLA-4 proteins, e.g., fusion proteins, described herein can be performed using protein production methods known in the art. For example, for scaled-up production, fermentation expression can be used.

Furthermore, although in a preferred embodiment the present methods use *P. pastoris* as a host organism, e.g., wild-type, X33, GS115 (his4), KM71, MC100-3, SMD1163, SMD1165, or SMD1168 strain, others can also be used. For example, mutant strains of *P. pastoris* that have been altered to express proteins with more human-like glycosylation can be used (see, e.g., Bollok et al., Recent Patents on Biotechnology 2009, 3, 192-201; U.S. Pat. Nos. 7,029,872; 6,803,225; 7,449,308; 7,252,933; 7,326,681; 7,507,573; and references described therein); in such methods, either the wild-type human CTLA-4 or the mutated human CTLA-4 can be used. Other yeast, e.g., other methylotropic yeast, e.g., yeast of the genera *Candida*, *Hansenula* or *Torulopsis*, can also be used. Generally speaking, most *P. pastoris* expression strains are derivatives of NRRL-Y 11430 (Northern Regional Research Laboratories, Peoria, Ill.).

Vectors suitable for use in the present methods are known in the art, and generally include a promoter, e.g., an AOX1, a constitutive *P. Pastoris* promoter derived from the *P. pastoris* glyceraldehyde-3-phosphate dehydrogenase gene (GAP) promoter, typically followed immediately with a DNA sequence that encodes a secretion signal, e.g., the *S. cerevisiae* α factor prepro signal sequence, or the signal sequence derived from the *P. pastoris* acid phosphatase gene (PHO1).

The vectors can also include one or more yeast selectable markers that can be used to identify and/or select those cells that contain the vector can be used. Such markers can include drug resistance markers and pathways for synthesis of essential cellular components, e.g., nutrients. Drug resistance markers that can be used in yeast include chloramphenicol, kanamycin, methotrexate, G418 (geneticin), Zeocin, and the like. Markers in synthesis pathways can be used with available yeast strains having auxotrophic mutations in the corresponding gene; examples include the pathways for synthesizing leucine (LEU2), tryptophan (TRP1 and TRP2), proline (PRO1), uracil (URA3, URA5, URA6), histidine (HIS3), lysine (LYS2), adenine (ADEJ or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al, J-Biol. Chem. 272:30061-30066 (1997)). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135). Examples of insertion sites include, but are not limited to, *Pichia* ADE genes; *Pichia* TRP (including TRP J through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al, Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X5 180. See e.g., WO2011046855; Cregg, J. M. (2007) *Methods in Molecular Biology: Pichia Protocols*, Second Edition, Volume 389, Humana Press, Totowa, N.J.; Romanos et al., Yeast 8:423-488 (1992); Ilgen, et al., (2004) Chapter 7: *Pichia pastoris*. In: *Production of recombinant proteins: microbial and eukaryotic expression systems*. Gellissen, G (ed.) Wiley-VCH Verlag, Weinheim, Germany, pp. 143-162; Cereghino and Cregg, FEMS Microbiology Reviews 24:45-66 (2000); and Cregg, "The *Pichia* System", available online at *pichia*.com/*pichia*_system.pdf. Exemplary vectors include pPIC3K, pPIC9K, pAO815 and the pPICZ vector series.

Purification

Methods known in the art can be used for nickel-based purification of the non-N-glycosylated human CTLA-4 proteins, e.g., fusion proteins. For example, although the present examples use a hexahistidine tag to facilitate purification, this may not be preferred for a pharmaceutical intended for in vivo use. Thus, other methods, including ammonium sulfate precipitation, reversed phase chromatography, hydrophobic interaction chromatography (HIC), size exclusion chromatography, ion exchange chromatography, affinity chromatography, metal binding, immunoaffinity chromatography, HPLC, or purification tags (e.g., as described above) may be used to directly capture the purified proteins. See, e.g., Deutscher, M. P. (1990) Guide to Protein Purification. In: *Methods in Enzymology* (J. N. Abelson and M. I. Simon, eds.) Academic Press, San Diego, Calif.; and *The Recombinant Protein Handbook, Protein Amplification and Simple Purification*, Amersham Biosciences, available online at 130.15.90.245/methods/handbooks%20and%20manuals/the%20recombinant%20protein%20handbook.pdf.

After purification, the protein can optionally be concentrated, e.g., by lyophilization or ultrafiltration.

Methods of Use

CTLA-4 proteins, e.g., recombinant non-N-glycosylated CTLA-4 or CTLA-4 fusion toxins, described herein can be used in the treatment of certain disorders, e.g., transplant rejection, proteinuria, or autoimmune disease, as well as cancers characterized by the presence of CD80/CD86-expressing cancer or tumor cells, e.g., CD80/CD86-expressing B-cell lymphomas. Generally, the methods include administering a therapeutically effective amount of CTLA-4 proteins, e.g., CTLA-4 fusion toxins, as described herein, alone or in combination with another active agent, to a subject who is in need of, or who has been determined to be in need of, such treatment.

Transplant Tolerance

The CTLA-4 proteins, e.g., CTLA-4 fusion toxins, described herein can be used to induce tolerance in a subject who is undergoing or who has undergone transplant with an allogeneic organ, tissue, or cells, e.g., a solid organ, tissue, bone marrow, or blood cells. For example, the methods can be used in a wide variety of tissue and organ transplant procedures, e.g., the methods can be used to induce tolerance in a recipient of a graft of stem cells such as bone marrow and/or of a tissue or organ such as pancreatic islets, liver, kidney, heart, lung, skin, muscle, neuronal tissue, stomach, and intestines. Thus, the new methods can be applied in treatments of diseases or conditions that entail stem cell tissue or organ transplantation (e.g., liver transplantation to treat liver failure, transplantation of muscle cells to treat muscular dystrophy, or transplantation of neuronal tissue to treat Huntington's disease or Parkinson's disease). In some embodiments, the methods include identifying, and then administering to, a subject in need of treatment. Tolerance to donor antigen can be evaluated by known methods, e.g., by MLR assays or cell-mediated lympholysis (CML) assays. In some embodiments, the methods include the use of the proteins or fusion proteins described herein to reduce ischemia/reperfusion injury associated with organ retrieval and storage influences the development of chronic graft dysfunction (Takada et al., J Clin Invest. 1997, 100(5):1199-203). In some embodiments, the proteins or fusion proteins are administered before, during, and/or after the transplant procedure.

Proteinuria/Minimal Change Disease

Minimal change disease is a nephrotic syndrome that has recently been linked to increased expression of CD80 on podocytes. CD80 expression on podocytes is regulated by CTLA-4 (see, e.g., Ishimoto et al., Semin Nephrol. July 2011; 31(4):320-5); thus, the recombinant non-N-glycosylated CTLA-4 proteins (i.e., the CTLA-4 proteins lacking a cytotoxic protein) described herein can be used to treat subjects suffering from minimal change disease, e.g., to reduce proteinuria.

Autoimmune Disease

Autoimmune disease as defined herein is a condition associated with unwanted production of antibodies to a self-antigen; in some embodiments, the methods result in a reduction in CD80+ (CD80 is also known as B7-1) and/or CD86+ (also known as B7-2) APCs, e.g., in the circulation of the subject. CTLA-4 has been implicated in the etiology and genetics of a number of autoimmune diseases, and blocking the CTLA-4:B7 costimulatory pathway has been shown to have therapeutic effect in models of multiple sclerosis, diabetes (e.g., insulin-dependent diabetes mellitus), systemic lupus erythematosus (SLE), and collagen-induced arthritis (Kristiansen et al., Genes and Immunity (2000) 1:170-184). Thus, in some embodiments the methods described herein can be used to treat subjects with autoimmune diseases, e.g., Rheumatoid arthritis (RA); Autoimmune thyroid diseases (AITD), e.g., Graves' disease (GD), Hashimoto's thyroiditis (HT), or Postpartum thyroiditis (PPT); Addison's disease (AD); Insulin-dependent diabetes mellitus (IDDM); Vitiligo; Myasthenia gravis (MG); Multiple sclerosis (MS); or Systemic lupus erythematosus (SLE) (see, e.g., Kristiansen et al., Genes and Immunity (2000) 1:170-184; Brunner-Weinzierl et al., Arthritis Res Ther. 2004; 6(2): 45-54).

B Cell Lymphoma

CD80 and CD86 are expressed on the surface of B cells in certain B-cell lymphomas; Dakappagari et al., Cytometry Part B: Clinical Cytometry. 82B(2):112-119, (2012); Suvas et al., J Biol Chem. (2002) 277:7766-7775. Thus, the CTLA-4 fusion toxins described herein can be used to target and deplete B cells expressing CD80 and/or CD86 in subjects. The methods can include detecting the presence of a B cell lymphoma characterized by the presence of cancerous B cells expressing CD80 and/or CD86. In some embodiments, the subject has non-Hodgkin's lymphoma (NHL), follicular lymphoma, diffuse large B cell lymphoma, mantle cell lymphoma, marginal zone lymphoma and small lymphocytic lymphoma. In some embodiments, the fusion toxins are used to target and deplete tumor infiltrating T cells in subjects with a lymphoma, e.g., NHL.

Pharmaceutical Compositions and Methods of Administration

The methods described herein include the manufacture and use of pharmaceutical compositions, which include CTLA-4 proteins, e.g., CTLA-4 fusion toxins, as described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Thus the present invention can include compositions comprising both a CTLA-4 proteins, e.g., CTLA-4 fusion toxins, as described herein and an additional active compound, e.g., in therapeutically relevant or effective amounts.

Pharmaceutical compositions are typically formulated to be compatible with the intended route of administration. Examples of routes of administration include parenteral, e.g., intravenous, intradermal, intramuscular, subcutaneous, oral (e.g., inhalation), transdermal (topical), and transmucosal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the Examples set forth below.

Porcine CTLA-4 (pCTLA-4) Plasmid Construction

According to the published amino acid sequence (UniProtKB/Swiss-Prot accession number: Q9MYX7), soluble porcine CTLA-4 DNA was synthesized using the *Pichia pastoris* preferred codons (Sreekrishna, K., 1993, Strategies for optimizing protein expression and secretion in the methylotrophic yeast *Pichia pastoris*. In Industrial Microorganism: Basic and Applied Molecular Genetics. R. H. Baltz, G.

D. Hegeman, and P. L. Skatrud, eds. American Society of Microbiology, Washington, D.C., pp. 119-126). Ten primers (Table 1) were designed to cover the full length of the soluble porcine CTLA-4 gene as well as its 6×His tag in the C-terminus (130 aa). There was a 21 base overlap between any of the neighboring primers. Ten pmol of the first and the last primer, and 2 pmol for the rest of the primers were used. The PCR program was conducted at 95° C. for 5 min, 25 cycles of 95° C. for 30 sec, 55° C. for 30 sec, 72° C. for 1 min and an extension at 72° C. for 10 min. The PCR products were analyzed with 1% agarose gel electrophoresis, and the band with the correct size cut out and extracted with QIAquick Gel Extraction Kit. The synthesized DNA was digested using XhoI and EcoRI and cloned into pwPICZα (FIG. 1) (Woo et al., 2002, Protein Expr. Purif. 25, 270-282). To facilitate the downstream purification, six histidines (6×His tag) were added at the C-terminus. To construct the non-N-glycosylated soluble porcine CTLA-4 two asparagines (potential N-linked glycosylation sites: N76A, N108A) were replaced with two non-polarized alanines using site-directed mutagenesis kit (Stratagene). The site-directed mutagenesis primers are listed in Table 1.

CTLA-4 Fusion Toxin Plasmid Construction

Codon optimization is necessary to express DT390-based fusion toxins in *Pichia pastoris* system (Woo et al 2002). A codon-optimized DT390 nucleotide sequence (Woo et al 2002) was used for the DT390 domain. The DT390 has been modified to include an $NH_2$ terminal alanine (A) and double mutations (dm) to prevent glycosylation in the eukaryotic expression system, *Pichia pastoris* (Woo et al 2002, Liu et al 2000). The codon-optimized glycosylated or non-N-glycosylated soluble porcine CTLA-4 nucleotide sequences described herein were used for the porcine CTLA-4 domain. The construct followed the strategy used to construct A-dm-DT390biscFv (2-6-15) in *Pichia pastoris* (Wang et al 2011). As shown in FIG. 8, the biscFv (2-6-15) was replaced using the codon-optimized glycosylated or non-N-glycosylated soluble porcine CTLA-4. Two codon-optimized non-N-glycosylated soluble porcine CTLA-4 was joined by $(G_4S)_3$ to form the bi-non-N-glycosylated porcine CTLA-4 version. To facilitate the downstream purification, six histidines (6×His tag) were added at the C-terminus.

Protein Expression in *Pichia pastoris*

TABLE 1

PCR primers used to synthesize glycosylated and non-N-glycosylated soluble porcine CTLA-4

| Primer Name | Sequence | SEQ ID NO: |
|---|---|---|
| CTL1 | 5' CCG CTC GAG AAG AGA GAG GCT GAA GCT ATG CAC GTT GCT CAA CCA GCT GTT GTC TTG 3' | 9 |
| CTL2 | 5' ACC GTA CTC ACA AAC GAA AGA AGC AAC ACC TCT AGA GTT AGC CAA GAC AAC AGC TGG TTG AGC 3' | 10 |
| CTL3 | 5' TCT TTC GTT TGT GAG TAC GGT TCT GCT GGT AAG GCT GCT GAG GTT AGA GTT ACT GTT TTG AGA 3' | 11 |
| CTL4 | 5' GTA AGT AGC AGC ACA AAC CTC AGT CAT TTG AGA ACC AGC TCT TCT CAA AAC AGT AAC TCT AAC 3' | 12 |
| CTL5 | 5' GAG GTT TGT GCT GCT ACT TAC ACT GTT GAG GAC GAG TTG ACT TTC TTG GAC GAC TCT ACT TGT 3' | 13 |
| CTL6 | 5' TTG AAT AGT CAA GTT AAC CTT GTT CTC AGT AGA AGT ACC AGT ACA AGT AGA GTC GTC CAA GAA 3' | 14 |
| CTL7 | 5' AAG GTT AAC TTG ACT ATT CAA GGT TTG AGA GCT GTC GAC ACC GGT TTG TAC ATC TGT AAG GTC 3' | 15 |
| CTL8 | 5' GTT ACC CAT ACC AAC GTA GTA TGG AGG TGG GTA CAA CAA TTC GAC CTT ACA GAT GTA CAA ACC 3' | 16 |
| CTL9 | 5' TAC TAC GTT GGT ATG GGT AAC GGT ACT CAA ATT TAC GTT ATT GAC CCT GAA CCA TGT CCT GAC 3' | 17 |
| CTL10 | 5' CCG GAA TTC TTA *GTG GTG GTG GTG GTG GTG* GTC AGA GTC AGG ACA TGG TTC AGG GTC 3' | 18 |
| For non-N-glycosylated soluble porcine CTLA4 DNA by site-directed mutagenesis: | | |
| N113A For | 5' ACT TCT ACT GAG AAC AAG GTT GCT TTG ACT ATT CAA GGT TTG AGA 3 | 19 |
| N113A Rev | 5' TCT CAA ACC TTG AAT AGT CAA AGC AAC CTT GTT CTC AGT AGA AGT 3' | 20 |
| N145A For | 5' CCA TAC TAC GTT GGT ATG GGT GCT GGT ACT CAA ATT TAC GTT ATT 3' | 21 |
| N145A Rev | 5' AAT AAC GTA AAT TTG AGT ACC AGC ACC CAT ACC AAC GTA GTA TGG 3' | 22 |

Approximately 5-10 µg of plasmid DNA for pCTLA-4 or pCTLA-4-fusion toxins (constructed as described above) were linearized by SacI digestion for 3 h at 37° C., treated with Qiagen PCR purification kit, and transformed into a diphtheria-toxin resistant yeast *Pichia pastoris* strain X33 or mutEF2JC307-8(2) (Liu et al 2003) using the GENE PULSER XCELL Electroporation system (Bio-Rad) and the transformants were selected on YPD plates containing zeocin (100 µg/ml) and incubated at 30° C. for 3-4 days. Six colonies were randomly picked and cultivated in small tubes containing 5 mL YPD (1% yeast extract, 2% peptone and 2% dextrose) at 30° C. at 250 rpm for 24 h as growth phase I, then in YPG (1% yeast extract, 2% peptone, 1% glycerol) at 30° C. at 250 rpm for another 24 h as growth phase II. The cultures were induced with methanol in 2 mL BMMYC (1% yeast extract, 2% peptone, 100 mM potassium phosphate, pH 7.0, 1.34% yeast nitrogen base without amino acids, $4 \times 10^{-5}$% biotin, 0.5% methanol and 1% casamino acids) for 48 h at 25° C. at 225 rpm. Antifoam 0.02% (Emerald Performance Materials, Cat# KFO673) was added in all of the growth and induction medium. 1 mM PMSF (Phenylmethanesulfonyl fluoride, Sigma) was added with methanol to inhibit the protein degradation during the induction phase. Additionally, 100 units/mL of penicillin and 100 µg/mL of streptomycin were also added to all of the growth and induction media to suppress bacterial contamination. The culture supernatants were analyzed on SDS-PAGE under non-reducing condition.

One clone for each construct was selected for large-scale expression. The large-scale expression was scaled-up from the small tube expression. The Excella E24 incubator shaker (New Brunswick) was employed to express the soluble porcine CTLA-4 or porcine CTLA-4 fusion toxins on a large-scale. The seed culture was prepared by inoculating a single colony into YPD medium, then incubating at 25° C., 225 rpm over the weekend. 5% of this seed culture was transferred to 1 L PYREX shake flasks containing 250 mL YPD medium and cultured at 30° C., 250 rpm for 24 h. Subsequently, cells were centrifuged at 1500 rpm for 5 minutes and the cell pellet was re-suspended in 250 mL YPG medium, and cultured at 30° C., 250 rpm for 24 h. For induction, cells were centrifuged at 1500 rpm for 5 minutes and the cell pellet was re-suspended in 125 mL BMMYC induction medium and induced at 25° C., 225 rpm. Following induction, 0.5% methanol was added twice daily (at 5 h, 24 h, and 30 h after initial induction) to sustain the methanol level. After 48 h induction, yeast cells were pelleted by centrifugation at 3000 rpm, 4° C. for 10 minutes. The supernatant containing the protein product could thereafter be purified. Antifoam, PMSF and penicillin/streptomycin were added to the media at the same concentrations as mentioned previously for the small-scale expression.

Protein Purification

Ni-Sepharose™ 6 fast flow resin was packed in a 5 cm×20 cm XK50 column (GE healthcare Cat#18-1000-71) for the first step purification. The column was equilibrated with 10 column volumes (CV) of 20 mM sodium phosphate pH 7.4, 0.5 M NaCl, and 5 mM imidazole. The sample was prepared by adding 0.5 M NaCl, 20 mM sodium phosphate pH 7.4, and 5 mM imidazole, filtered through crepe fluted filter paper (VWR) and loaded onto the equilibrated column. The column was washed using 6 CV of 20 mM sodium phosphate pH 7.4, 0.5 M NaCl, and 5 mM imidazole. The bound proteins were eluted with 20 mM sodium phosphate pH 7.4, 0.5 M NaCl, 500 mM imidazole for porcine CTLA-4 fusion toxins or 100 mM, then 200 mM imidazole for soluble porcine CTLA-4 into eight fractions each. The purification fractions were analyzed using 4-12% or 12% NuPAGE® Bis-Tris gel and stained with GelCode Blue stain reagent (Thermo Scientific). The fractions containing the bound protein of interest were pooled and dialyzed using a 3.5 kDa cut off Spectra/Por® membrane tubing (Spectrumlabs) against 4 L of 20 mM Tris-HCl pH 8.0, 1 mM EDTA pH 8.0, 5% glycerol at 4° C. with constant stirring. The dialysis buffer was replaced once.

Strong anion exchange resin Poros® 50 HQ (Applied Biosystems) in a XK16/20 column (GE Healthcare) was applied for the second step purification. The column was equilibrated with 20 mM Tris-HCl pH 8.0, 1 mM EDTA, 5% glycerol (10 CV). The above dialyzed sample was loaded into the column and washed with 20 mM Tris-HCl pH 8.0, 1 mM EDTA, 5% glycerol (8 CV). The bound protein was eluted with either 200 mM sodium borate and then 200 mM sodium borate+50 mM NaCl in 20 mM Tris-HCl pH 8.0, 1 mM EDTA, 5% glycerol (for the CTLA-4 fusion toxins) or 100 then 200 mM sodium borate in 20 mM Tris-HCl pH 8.0, 1 mM EDTA, 5% glycerol (for the pCTLA-4) into eight fractions each. The purified fractions were analyzed using 4-12% or 12% NuPAGE Bis-Tris SDS gel. Protein concentration was determined using Pierce BCA protein assay kit (Thermo Scientific). The endotoxin level was measured using The Endosafe-PTS Portable Test System (Charles River Laboratories)

Western Blotting

Protein samples were separated by electrophoresis using NuPAGE 12% Bis-Tris Gel and the gel electro-transferred at 35 V onto a nitrocellulose membrane filter paper using 1× NuPAGE® transfer buffer (Invitrogen). The membrane was thereafter blocked in 5% non-fat dry milk (Bio-Rad) in 1×PBS, 0.02% Tween 20 for 1 h with shaking and then washed once with 1×PBS, pH7.4, 0.02% Tween 20 at room temperature with shaking. The soluble porcine CTLA-4 or porcine CTLA-4 fusion toxin was detected with mouse anti-His monoclonal antibody (1.11 μg/mL) (Invitrogen) and rat anti-mouse IgG-HRP (1.25 μg/mL) (Invitrogen) in 5% non-fat dry milk in 1×PBS, 0.02% Tween 20. The soluble porcine CTLA-4 or porcine CTLA-4 fusion toxin was detected with mouse anti-His monoclonal antibody (1.11 μg/mL) (Invitrogen) and rat anti-mouse IgG-HRP (1.25 μg/mL) (Invitrogen) in 5% non-fat dry milk in 1×PBS, 0.02% Tween 20. Detection of the proteins was done by TMB membrane peroxidase substrate (KPL Cat#:50-77-02), and color development was stopped with $dH_2O$.

Protein Synthesis Inhibition Assay

Porcine CTLA-4 fusion toxins (DT390-pCTLA-4-Gly, DT390-pCTLA-4-Non-N-Gly, and DT390-bi-pCTLA-4-Non-N-Gly) were diluted to $10^{-6}$, $10^{-8}$, $10^{-10}$, $10^{-12}$, $10^{-14}$ and $10^{-16}$ M in 1× leucine-free RPMI 1640 media supplemented with 12% fetal bovine serum (FBS), 10 mM hepes (N-2-hydroxyethylpiperazine-N-2-ethanesulfonic acid), 1× nonessential amino acids, 1 mM sodium pyruvate, 2 mM glutamine, and $2.5\times10^{-5}$ M 2-mercaptoethanol Ten microliters of fusion toxin dilutions were added to each well (three wells per dilution) in a 96-well flat bottom plate (Corning). Cells from the porcine B-cell lymphoma cell line 13271-5E4 were washed twice by centrifugation at 1000 rpm, 20° C. for 5 minutes in 50 mL of leucine-free RPMI 1640 media described above. Cells were then diluted to $5.0\times10^5$ cells/mL in leucine-free RPMI 1640 media and 100 μL of cells was added to each well containing the fusion toxin to achieve a final cell concentration of $5.0\times10^4$ cells/mL. Six wells contained only cells, three of these remained without fusion toxin and served as the negative control and the other three were reserved for the positive control which was added later.

Plates were then incubated at 37° C. with 5% $CO_2$ for 18 hours. Cyclohexamide (Invitrogen) was diluted 1:8 and 10 μL of this dilution was added to each of three wells containing cells only then incubated for the last 15 min. of the 18 hr. incubation. Cells were pulsed with 1 μCi/well of $^3$H-Leucine then incubated at 37° C. with 5% $CO_2$ for 1 hour. Cells were harvested onto filter mats (Perkin-Elmer) using a cell harvester (Harvester 96® Mach II). The filters were allowed to dry at room temperature overnight then CCPM was measured on a microbeta counter.

Biotin-Labeling of the pCTLA-4 and pCTLA-4 Fusion Toxins

Glycosylated or non-N-glycosylated soluble porcine CLTA-4 or porcine CLTA-4 fusion toxin was labeled with EZ-Link Sulfo-NHS Biotin (Pierce, Cat#21217). One milligram of NHS-Biotin was added to one milligram of purified protein, and then the reaction was incubated for 2 hours at 4° C. with rocking. The reaction was transferred to a Slide-a-lyzer dialysis cassette, 10K MWCO, 0.5-3 mL (Thermo Fisher Cat#66380) and dialyzed against 2 L of 1×PBS for 24 hours at 4° C. with constant stirring, changed once.

Screening pCTLA-4 Porcine CD80-Expressing B-Cell Lymphoma Cell Line

Porcine B-cell lymphoma tumor cell lines available in our laboratory (Cho et al., Blood, 110, 3996-4004 (2007)) were cultured in T75 culture flasks (Corning, Cat#10-126-31) with 1×RPMI 1640 media supplemented with 12% fetal bovine serum, 10 mM hepes (N-2-hydroxyethylpiperazine-N-2-ethanesulfonic acid), 1× nonessential amino acids, 1 mM sodium pyruvate, 2 mM glutamine, and $2.5 \times 10^{-5}$M 2-mercaptoethanol. Cultures were incubated at 37° C. with 5% $CO_2$ until a cell density of $1.0 \times 10^6$ cells/mL was achieved. Cells were spun down and re-suspended to a concentration of $1.0 \times 10^7$ cells/mL in FACS media containing 1× Hanks Balanced Salt Solution with $Ca^+$ and $Mg^+$, 0.1% Bovine serum albumin and 0.1% sodium azide and aliquotted into FACS tubes at $1.0 \times 10^6$ cells/tube. Biotin-labeled hamster anti-mouse CD80 mAb clone 16-10A1 (BioLegend, Cat#104703) was then added to each cell line at a final concentration of 17 nM and cells were incubated at 4° C. for 30 minutes. Cells were washed twice with 2 mL FACS media and centrifuged at 1200 rpm, 4° C. for 5 minutes. Streptavidin-PE was added to each tube at a final concentration of 1.5 ng/uL and incubated in the dark at 4° C. for 15 minutes. Cells were then washed once as described above then re-suspended in 500 μL of FACS media and flow cytometry was carried out using a Becton Dickinson FACScan. Flow cytometry data were analyzed using Winlist analysis software (Verity Software House, Topsham, Me.). Human CD80-expressing leukemia cell line THP-1 was used as the hamster anti-mouse CD80 mAb positive control cell line.

FACS Binding Analysis of pCTLA-4 and Porcine CTLA-4 Fusion Toxins to Porcine CD80

Porcine CD80-expressing B-cell lymphoma cell line LCL13271-5E4 (Cho et al 2007) as well as the control human CD80-expressing leukemia cell line THP-1 were cultured and stained as described above. Cells were stained with biotinylated glycosylated or non-N-glycosylated soluble porcine CTLA-4 or porcine CTLA-4 fusion toxin at a range of dilutions. Biotin-labeled hamster anti-mouse CD80 mAb clone 16-10A1 (BioLegend, Cat#104703) used at a final concentration of 17 nM as positive staining control. Negative control cells were stained only with streptavidin-PE at a final concentration of 1.5 ng/uL (without biotylated soluble porcine CTLA-4 or porcine CTLA-4 fusion toxin).

Flow cytometry was carried out using a Becton Dickson FACScan. Flow cytometry data were analyzed using Winlist analysis software (Verity Software House, Topsham, Me.).

$K_D$ Determination

FACS binding analysis of porcine CTLA-4 and pCTLA-4 fusion toxins were performed using the porcine CD80-expressing porcine B cell lymphoma line LCL13271-5E4 with a wide range concentrations of biotinylated soluble porcine CTLA-4 or porcine CTLA-4 fusion toxin. The mean fluorescence intensity (MFI) values were tabulated and plotted on a linear scale versus each biotinylated soluble porcine CTLA-4 or porcine CTLA-4 fusion toxin concentration. This plot was fitted using non-linear least-squares by KaleidaGraph software (Synergy Software, Reading Pa.) using the hyperbolic equation $y = m1 + m2 \ast m0/(m3 + m0)$, where y=MFI at the given biotinylated protein concentration, m0=biotinylated protein concentration, m1=MFI of zero biotinylated protein control, m2=MFI at saturation and m3=$K_D$, the equilibrium dissociation constant (Yeast Display scFv Antibody Library User's Manual, Pacific Northwest National Laboratory, Richland, Wash.; Revision Date: MF031112, available at sysbio.org/dataresources/index.stm)

Example 1. Expression and Purification of Glycosylated Soluble Porcine CTLA-4 in *Pichia pastoris*

A codon-optimized soluble porcine CTLA-4 DNA carrying 6×His tag (130aa) in the C-terminus was synthesized and cloned into *Pichia pastoris* expression vector pwPICZα (FIG. 1) (Woo et al., 2002, Protein Expr. Purif. 25, 270-282). A 6×His tag in the C-terminus was added to facilitate the downstream purification.

The codon-optimized N-glycosylated soluble porcine CTLA-4 DNA and amino acid sequence (aa 38-161, 124 aa+6×His) were as follows:

```
                                           SEQ ID NO: 23
                                           SEQ ID NO: 24
atgcacgttgctcaaccagctgttgtcttggctaactctagaggtgttg
 M   H   V   A   Q   P   A   V   V   L   A   N   S   R   G   V
cttctttcgtt
 A   S   F   V tgtgagtacggttctgctggtaaggctgctgaggttagagttactgttt
 C   E   Y   G   S   A   G   K   A   A   E   V   R   V   T   V
tgagaagagct
 L   R   R   A ggttctcaaatgactgaggtttgtgctgctacttacactgttgaggacg
 G   S   Q   M   T   E   V   C   A   A   T   Y   T   V   E   D
agttgactttc
 E   L   T   F ttggacgactctacttgtactggtacttctactgagaacaaggttaact
 L   D   D   S   T   C   T   G   T   S   T   E   N   K   V   N
tgactattcaa
 L   T   I   Q ggtttgagagctgtcgacaccggtttgtacatctgtaaggtcgaattgt
 G   L   R   A   V   D   T   G   L   Y   I   C   K   V   E   L
tgtacccacct
 L   Y   P   P ccatactacgttggtatgggtaacggtactcaaatttacgttattgacc
 P   Y   Y   V   G   M   G   N   G   T   Q   I   Y   V   I   D
ctgaaccatgt
 P   E   P   C cctgactctgaccaccaccaccaccaccac
 P   D   S   D   H   H   H   H   H   H
```

The DNA construct was linearized and transformed into *Pichia pastoris* strain X33. Soluble porcine CTLA-4 carrying 6×His in the C-terminus was expressed using the large-scale shake-flask system as described in materials and methods. Western blotting analysis confirmed the expression using mouse anti-His monoclonal antibody. The secreted soluble porcine CTLA-4 was captured directly by Ni-Sepharose 6 fast flow resin through its 6×His-tag in the C-terminus (FIG. 2A). The eluted fractions from the capturing step were pooled, concentrated with Centricon Plus-70 (5 kDa cut off) and dialyzed to remove the salts for the second step purification. Based on the PI value (5.33) strong anion exchange resin Poros 50 HQ was used for the second step purification. In which, sodium borate was applied to separate the porcine CTLA-4 from the glycosylated yeast host protein and aggregates (Woo et al., 2003, BioTechniques 35, 392-398). As shown in FIG. 2B (elution fractions with 200 mM sodium borate) soluble porcine CTLA-4 was obtained after this two-step purification. The final product level was ~2 mg/L (Table 2) with an assessed endotoxin level of <13.5 EU/mg.

TABLE 2

Comparison of expression and purification levels for the glycosylated and non-N-glycosylated soluble porcine CTLA-4

| Purification step | Glycosylated (Recovery %) | Non-N-Glycosylated (Recovery %) |
|---|---|---|
| Supernatant | ~5 mg/L (100%) | ~20 mg/L (100%) |
| Ni-Sepharose 6 fast flow | ~3 mg/L (60%) | ~16 mg/L (80%) |
| Poros 50 HQ | ~2 mg/L (40%) | ~8 mg/L (40%) |

Example 2. Expression and Purification of Non-N-Glycosylated Soluble Porcine CTLA-4 in *Pichia Pastoris*

As shown in FIG. 3, N-linked glycosylation analysis using PNGase F digestion demonstrated that the *Pichia pastoris* expressed soluble porcine CTLA-4 was N-glycosylated completely or partially. The protein expression level was low and the final product was not well purified as shown in FIG. 2B (elution fractions with 200 mM sodium borate). Using this approach it would be difficult to scale up to produce enough pure and cost-effective soluble porcine CTLA-4 for clinical use or for a porcine transplantation model. It was hypothesized that N-glycosylation may be responsible for the low expression level and the difficulty of purification. If the potential N-glycosylation sites were mutated and the soluble porcine CTLA-4 still maintained its original binding function, it may be possible to improve the expression level and facilitate a more effective purification. The two potential N-glycosylation sites were replaced with non-polarized alanines by site-directed mutagenesis (Stratagene).

The codon-optimized non-N-glycosylated soluble porcine CTLA-4 DNA and amino acid sequence (aa 38-161, 124 aa+6×His) were as follows; sites mutated to alanine to remove N-linked glycosylation are in bold:

SEQ ID NO: 25
SEQ ID NO: 26

```
atgcacgttgctcaaccagctgttgtcttggctaactctagaggtg
 M   H   V   A   Q   P   A   V   V   L   A   N   S   R   G
ttgcttctttcgtt
 V   A   S   F   V
tgtgagtacggttctgctggtaaggctgctgaggttagagttactg
 C   E   Y   G   S   A   G   K   A   A   E   V   R   V   T
ttttgagaagagct
 V   L   R   R   A
ggttctcaaatgactgaggtttgtgctgctacttacactgttgagg
 G   S   Q   M   T   E   V   C   A   A   T   Y   T   V   E
acgagttgactttc
 D   E   L   T   F
ttggacgactctacttgtactggtacttctactgagaacaaggttg
 L   D   D   S   T   C   T   G   T   S   T   E   N   K   V
ctttgactattcaa
 A   L   T   I   Q
ggtttgagagctgtcgacaccggtttgtacatctgtaaggtcgaat
 G   L   R   A   V   D   T   G   L   Y   I   C   K   V   E
tgttgtacccacct
 L   L   Y   P   P
ccatactacgttggtatgggtgctggtactcaaatttacgttattg
 P   Y   Y   V   G   M   G   A   G   T   Q   I   Y   V   I
accctgaaccatgt
 D   P   E   P   C
cctgactctgaccaccaccaccaccaccac
 P   D   S   D   H   H   H   H   H   H
```

As shown in FIGS. 4A, B and C, a very pure non-N-glycosylated soluble porcine CTLA-4 was obtained after two step purification and the production level was improved to ~8 mg/L (Table 2). The endotoxin concentration is <14.2 EU/mg. This facilitates large scale production of pure non-N-glycosylated soluble porcine CTLA-4 suitable for clinical use or for use in a porcine transplantation model.

Figure 5B:
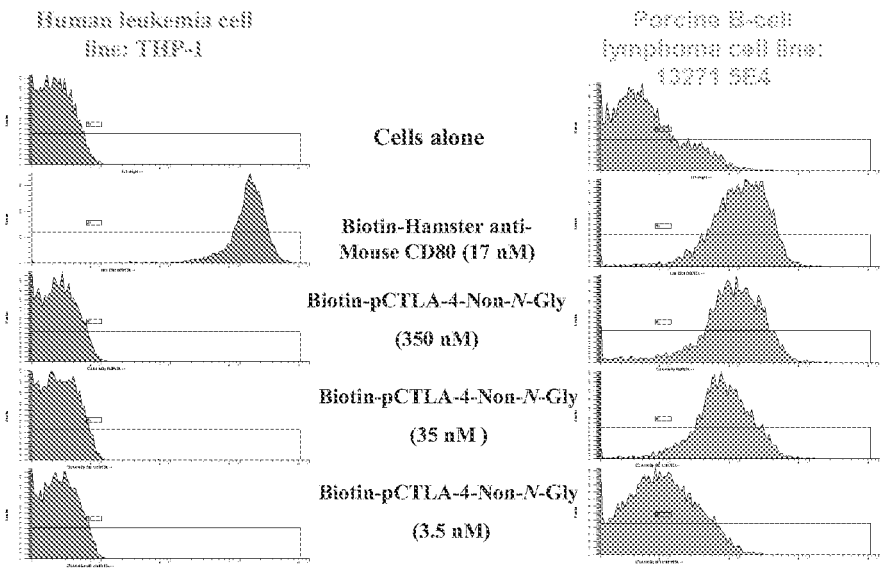

Example 3. FACS Analysis for Binding to Porcine CD80 Using a Porcine CD80-Expressing B-Cell Lymphoma Cell Line Porcine CTLA-4 binds to porcine CD80 and CD86 in nature. Therefore a CD80- or CD86-expressing porcine antigen presenting cell line is required in order to assess the binding function of the soluble porcine CTLA-4 in vitro. Using FACS analysis with hamster anti-mouse CD80 mAb (clone 16-10A1) (BioLegend, Cat#104703) a porcine CD80-expressing B-cell lymphoma cell line (LCL13271-5E4) was successfully screened from available potential porcine B-cell lymphoma cell lines (Cho et al., 2007, Blood, 110, 3996-4004). As shown in FIGS. 5A and 5B, FACS binding analysis demonstrated that both biotinylated glycosylated and non-N-glycosylated soluble porcine CTLA-4 bound to the porcine CD80-expressing B-cell lymphoma cell line LCL13271-5E4 in a dose-dependent manner. No binding to the human CD80-expressing leukemia cell line THP-1 was detected indicating that binding is species specific. To confirm the specific binding of the soluble porcine CTLA-4 to porcine CD80, a dose-dependent blocking/competition assay for the binding of hamster anti-mouse CD80 mAb (clone 16-10A1) to the porcine CD-80 expressing B-cell lymphoma cell line (LCL13271-5E4) was also performed using the non-biotinylated glycosylated or non-N-glycosylated soluble porcine CTLA-4. As shown in FIGS. 6A and 6B, both glycosylated and non-N-glycosylated soluble porcine CTLA-4 blocked the binding in a dose-dependent manner. Therefore both glycosylated and non-N-glycosylated soluble porcine CTLA-4 are biologically functional in vitro. These results also indicate that the binding epitope/domain of the soluble porcine CTLA-4 and the hamster anti-mouse CD80 mAb on the porcine B-cell lymphoma cell line is same or overlapped.

Figure 7A:
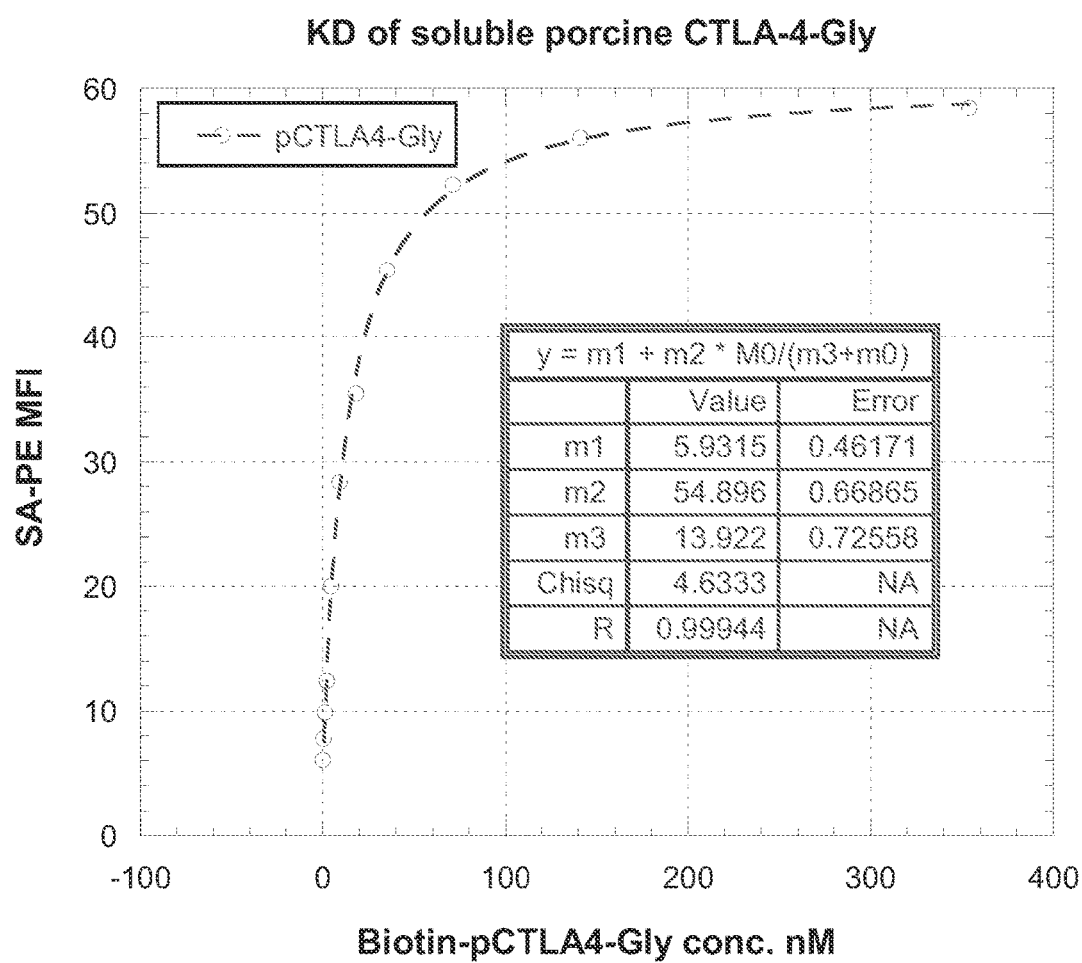
Figure 7B:
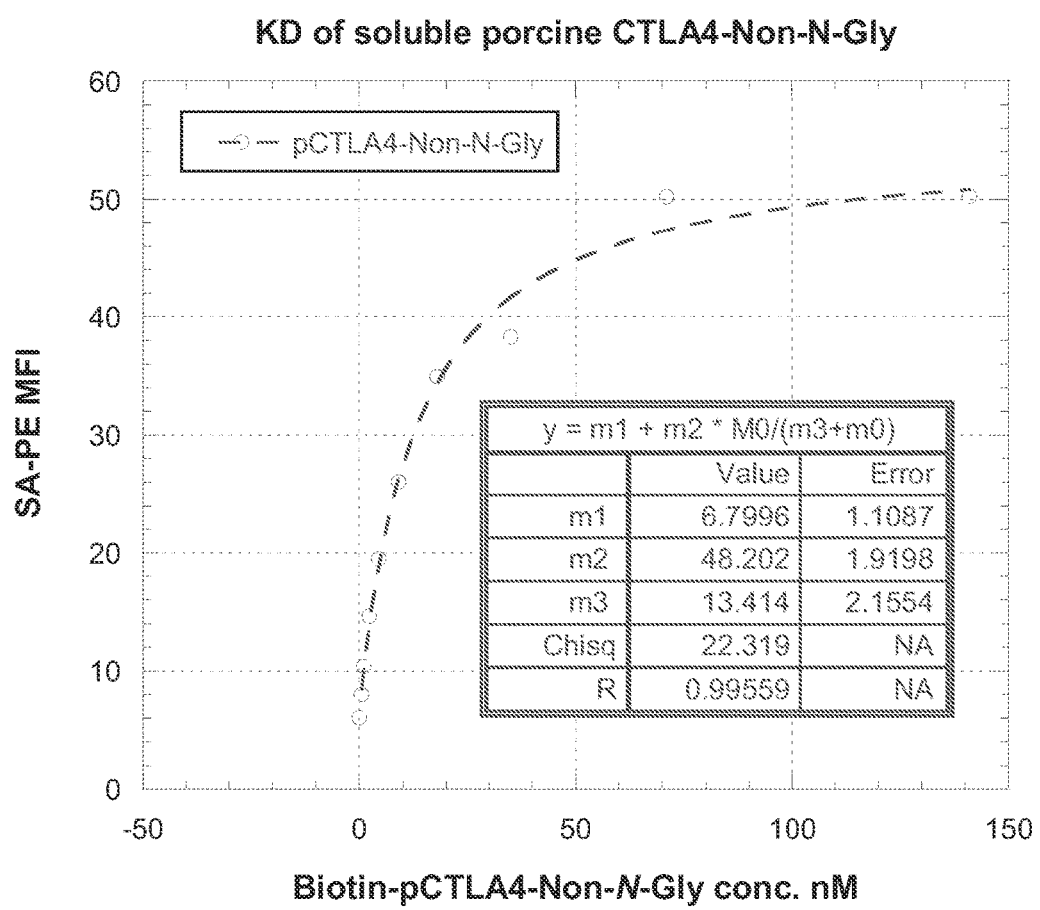

As shown in FIGS. 7A-B, the $K_D$ value was determined by plotting the FACS-MFI values versus a wide range of concentrations of the biotinylated glycosylated or non-N-glycosylated soluble porcine CTLA-4. The non-linear least-squares curve fitting revealed a $K_D$ of 13 nM (m3 value of the inset table in FIGS. 7A and 7B) for both glycosylated and non-N-glycosylated soluble porcine CTLA-4.

Example 4. Plasmid Construction for the Porcine CTLA-4 Fusion Toxins

Porcine CTLA-4 fusion toxin was composed with two domains: 1) the truncated diphtheria toxin DT390 and 2) soluble porcine CTLA-4. The codon-optimized glycosylated or non-N-glycosylated soluble porcine CTLA-4 DNA was cloned into the truncated diphtheria toxin DT390 containing yeast *Pichia pastoris* expression vector pwPICZalpha-A-dmDT390 between NcoI and EcoRI to replace the biscFv (2-6-15) portion (Wang et al 2011). To facilitate the downstream purification a 6xHis tag was added to the C-terminus of the construct. As shown in FIG. 8 three versions of the porcine CTLA-4 fusion toxin were constructed: 1) single glycosylated soluble porcine CTLA-4 version (DT390-pCTLA-4-Gly); 2) single non-N-glycosylated soluble porcine CTLA-4 version (DT390-pCTLA-4-Non-N-Gly) and 3) bi-non-N-glycosylated soluble porcine CTLA-4 version (DT390-bi-pCTLA-4-Non-N-Gly). The bi-non-N-glycosylated soluble porcine CTLA-4 was joined by a $(G_4S)_3$ linker. There is a $G_4S$ linker between DT390 domain and porcine CTLA-4 domain.

The amino acid and DNA sequence for the three versions of DT390-pCTLA-4 fusion toxin were as follows:

```
1) DT390-pCTLA-4-Gly-6xHis (amino acid sequence)
Underlined, DT390 domain. Double underlined, porcine CTLA-4 domain.
Plain, G4S linker
                                                            (SEQ ID NO: 4)
        10         20         30         40         50         60
AGADDVVDSS KSFVMENFAS YHGTKPGYVD SIQKGIQKPK SGTQGNYDDD WKGFYSTDNK 70         80         90        100        110        120
YDAAGYSVDN ENPLSGKAGG VVKVTYPGLT KVLALKVDNA ETIKKELGLS LTEPLMEQVG 130        140        150        160        170        180
TEEFIKRFGD GASRVVLSLP FAEGSSSVEY INNWEQAKAL SVELEINFET RGKRGQDAMY 190        200        210        220        230        240
EYMAQACAGN RVRRSVGSSL SCINLDWDVI RDKTKTKIES LKEHGPIKNK MSESPAKTVS 250        260        270        280        290        300
EEKAKQYLEE FHQTALEHPE LSELKTVTGT NPVFAGANYA AWAVNVAQVI DSETADNLEK 310        320        330        340        350        360
TTAALSILPG IGSVMGIADG AVHHNTEEIV AQSIALSSLM VAQAIPLVGE LVDIGFAAYN 370        380        390        400        410        420
FVESIINLFQ VVHNSYNRPA YSPGHKTQPF LPWGGGGSMH VAQPAVVLAN SRGVASFVCE 430        440        450        460        470        480
YGSAGKAAEV RVTVLRRAGS QMTEVCAATY TVEDELTFLD DSTCTGTSTE NKVNLTIQGL 490        500        510        520
RAVDTGLYIC KVELLYPPPY YVGMGNGTQI YVIDPEPCPD SDHHHHHH 1) DT390-pCTLA-4-Gly-6xHis (DNA sequence)
Underlined, DT390 domain. Double underlined, porcine CTLA-4 domain.
Plain, NcoI recognition site (CCA TGG) and G4S linker
                                                            (SEQ ID NO: 27)
GCTGGTGCTGACGACGTCGTCGACTCCTCCAAGTCCTTCGTCATGGAGAAC

TTCGCTTCCTACCACGGGACCAAGCCAGGTTACGTCGACTCCATCCAGAA

GGGTATCCAGAAGCCAAAGTCCGGCACCCAAGGTAACTACGACGACGACT

GGAAGGGGTTCTACTCCACCGACAACAAGTACGACGCTGCGGGATACTCT

GTAGATAATGAAAACCCGCTCTCTGGAAAAGCTGGAGGCGTGGTCAAGGT

CACCTACCCAGGTCTGACTAAGGTCTTGGCTTTGAAGGTCGACAACGCTG

AGACCATCAAGAAGGAGTTGGGTTTGTCCTTGACTGAGCCATTGATGGAG

CAAGTCGGTACCGAAGAGTTCATCAAGAGATTCGGTGACGGTGCTTCCAG

AGTCGTCTTGTCCTTGCCATTCGCTGAGGGTTCTTCTAGCGTTGAATATATT

AATAACTGGGAACAGGCTAAGGCTTTGTCTGTTGAATTGGAGATTAACTT

CGAAACCAGAGGTAAGAGAGGTCAAGATGCGATGTATGAGTATATGGCTC

AAGCCTGTGCTGGTAACAGAGTCAGACGTTCTGTTGGTTCCTCTTTGTCCT

GTATCAACCTAGACTGGGACGTCATCAGAGACAAGACTAAGACCAAGATC
```

-continued

GAGTCTTTGAAAGAGCATGGCCCAATCAAGAACAAGATGTCCGAATCCCC

CGCTAAGACCGTCTCCGAGGAAAAGGCCAAGCAATACCTAGAAGAGTTCC

ACCAAACCGCCTTGGAGCATCCTGAATTGTCAGAACTTAAAACCGTTACT

GGGACCAATCCTGTATTCGCTGGGGCTAACTATGCGGCGTGGGCAGTAAA

CGTTGCGCAAGTTATCGATAGCGAAACAGCTGATAATTTGGAAAAGACAA

CTGCTGCTCTTTCGATACTTCCTGGTATCGGTAGCGTAATGGGCATTGCAG

ACGGTGCCGTTCACCACAATACAGAAGAGATAGTGGCACAATCCATCGCT

TTGTCCTCTTTGATGGTTGCTCAAGCTATCCCATTGGTCGGTGAGTTGGTT

GACATCGGTTTCGCTGCCTACAACTTCGTCGAGTCCATCATCAACTTGTTC

CAAGTCGTCCACAACTCCTACAACCGTCCGGCTTACTCCCCAGGTCACAA

GACCCAACCATTCTTGCCATGG GGT GGT GGT GGT TCT ATG CAC GTT

GCT CAA CCA GCT GTT GTC TTG GCT AAC TCTAGA GGT GTT GCT TCT

TTC GTT TGT GAG TACGGT TCT GCT GGT AAG GCT GCT GAG GTT AGA

GTT ACT GTT TTG AGA AGA GCT GGT TCT CAAATG ACT GAG GTT TGT

GCT GCT ACT TAC ACTGTT GAG GAC GAG TTG ACT TTC TTG GAC GAC

TCT ACT TGT ACT GGT ACT TCT ACT GAG AAC AAG GTT AAC TTG ACT

ATT CAA GGT TTG AGAGCT GTC GAC ACC GGT TTG TAC ATC TGT AAG

GTC GAA TTG TTG TAC CCA CCT CCA TAC TACGTT GGT ATG GGT AAC

GGT ACT CAA ATT TACGTT ATT GAC CCT GAA CCA TGT CCT GAC TCT

GAC CAC CAC CAC CAC CAC CAC

2) DT390-pCTLA4-Non-N-Gly-6xHis (amino acid sequence)
Underlined, DT390 domain. Double underlined, porcine CTLA-4 domain.
Bold italics, mutated residues (SEQ ID NO: 2)

```
        10         20         30         40         50         60
AGADDVVDSS KSFVMENFAS YHGTKPGYVD SIQKGIQKPK SGTQGNYDDD WKGFYSTDNK 70         80         90        100        110        120
YDAAGYSVDN ENPLSGKAGG VVKVTYPGLT KVLALKVDNA ETIKKELGLS LTEPLMEQVG 130        140        150        160        170        180
TEEFIKRFGD GASRVVLSLP FAEGSSSVEY INNWEQAKAL SVELEINFET RGKRGQDAMY 190        200        210        220        230        240
EYMAQACAGN RVRRSVGSSL SCINLDWDVI RDKTKTKIES LKEHGPIKNK MSESPAKTVS 250        260        270        280        290        300
EEKAKQYLEE FHQTALEHPE LSELKTVTGT NPVFAGANYA AWAVNVAQVI DSETADNLEK 310        320        330        340        350        360
TTAALSILPG IGSVMGIADG AVHHNTEEIV AQSIALSSLM VAQAIPLVGE LVDIGFAAYN 370        380        390        400        410        420
FVESIINLFQ VVHNSYNRPA YSPGHKTQPF LPWGGGGSMH VAQPAVVLAN SRGVASFVCE 430        440        450        460        470        480
YGSAGKAAEV RVTVLRRAGS QMTEVCAATY TVEDELTFLD DSTCTGTSTE NKVALTIQGL 490        500        510        520
RAVDTGLYIC KVELLYPPPY YVGMGAGTQI YVIDPEPCPD SDHHHHHH
```

2) DT390-pCTLA4-Non-N-Gly-6xHis (DNA sequence)
Underlined, DT390 domain. Double underlined, porcine CTLA-4 domain.
Bold italics, mutated residues. Plain, NcoI recognition site
(CCA TGG) and $G_4S$ linker (SEQ ID NO: 28)

GCT GGT GCT GAC

GACGTCGTCGACTCCTCCAAGTCCTTCGTCATGGAGAACTTCGCTTCCTAC

-continued

CACGGGACCAAGCCAGGTTACGTCGACTCCATCCAGAAGGGTATCCAGAA

GCCAAAGTCCGGCACCCAAGGTAACTACGACGACGACTGGAAGGGGTTCT

ACTCCACCGACAACAAGTACGACGCTGCGGGATACTCTGTAGATAATGAA

AACCCGCTCTCTGGAAAAGCTGGAGGCGTGGTCAAGGTCACCTACCCAGG

TCTGACTAAGGTCTTGGCTTTGAAGGTCGACAACGCTGAGACCATCAAGA

AGGAGTTGGGTTTGTCCTTGACTGAGCCATTGATGGAGCAAGTCGGTACC

GAAGAGTTCATCAAGAGATTCGGTGACGGTGCTTCCAGAGTCGTCTTGTC

CTTGCCATTCGCTGAGGGTTCTTCTAGCGTTGAATATATTAATAACTGGGA

ACAGGCTAAGGCTTTGTCTGTTGAATTGGAGATTAACTTCGAAACCAGAG

GTAAGAGAGGTCAAGATGCGATGTATGAGTATATGGCTCAAGCCTGTGCT

GGTAACAGAGTCAGACGTTCTGTTGGTTCCTCTTTGTCCTGTATCAACCTA

GACTGGGACGTCATCAGAGACAAGACTAAGACCAAGATCGAGTCTTTGAA

AGAGCATGGCCCAATCAAGAACAAGATGTCCGAATCCCCCGCTAAGACCG

TCTCCGAGGAAAAGGCCAAGCAATACCTAGAAGAGTTCCACCAAACCGCC

TTGGAGCATCCTGAATTGTCAGAACTTAAAACCGTTACTGGGACCAATCCT

GTATTCGCTGGGGCTAACTATGCGGCGTGGGCAGTAAACGTTGCGCAAGT

TATCGATAGCGAAACAGCTGATAATTTGGAAAAGACAACTGCTGCTCTTT

CGATACTTCCTGGTATCGGTAGCGTAATGGGCATTGCAGACGGTGCCGTTC

ACCACAATACAGAAGAGATAGTGGCACAATCCATCGCTTTGTCCTCTTTG

ATGGTTGCTCAAGCTATCCCATTGGTCGGTGAGTTGGTTGACATCGGTTTC

GCTGCCTACAACTTCGTCGAGTCCATCATCAACTTGTTCCAAGTCGTCCAC

AACTCCTACAACCGTCCGGCTTACTCCCCAGGTCACAAGACCCAACCATTC

TTG GGT GGT GGT GGT TCT ATG CAC GTT GCT CAA CCA GCT GTT GTC

TTG GCT AAC TCT AGA GGT GTT GCT TCT TTC GTT TGT GAG TAC GGT

TCT GCT GGT AAG GCT GCT GAG GTT AGA GTT ACT GTT TTG AGA AGA

GCT GGT TCT CAA ATG ACT GAG GTT TGT GCT GCT ACT TAC ACT GTT

GAG GAC GAG TTG ACT TTC TTG GAC GAC TCT ACT TGT ACT GGT ACT

TCT ACT GAG AAC AAG GTT *GCT* TTG ACT ATT CAA GGT TTG AGA GCT

GTC GAC ACC GGT TTG TAC ATC TGT AAG GTC GAA TTG TTG TAC CCA

CCT CCA TAC TAC GTT GGT ATG GGT *GCT* GGT ACT CAA ATT TAC GTT

ATT GAC CCT GAA CCA TGT CCT GAC TCT GAC CAC CAC CAC CAC CAC

CAC

3) DT390-bi-pCTLA-4-Non-N-Gly-6xHis (amino acid sequence):

(SEQ ID NO: 3)

```
        10         20         30         40         50         60
AGADDVVDSS KSFVMENFAS YHGTKPGYVD SIQKGIQKPK SGTQGNYDDD WKGFYSTDNK 70         80         90        100        110        120
YDAAGYSVDN ENPLSGKAGG VVKVTYPGLT KVLALKVDNA ETIKKELGLS LTEPLMEQVG 130        140        150        160        170        180
TEEFIKRFGD GASRVVLSLP FAEGSSSVEY INNWEQAKAL SVELEINFET RGKRGQDAMY 190        200        210        220        230        240
EYMAQACAGN RVRRSVGSSL SCINLDWDVI RDKTKTKIES LKEHGPIKNK MSESPAKTVS 250        260        270        280        290        300
EEKAKQYLEE FHQTALEHPE LSELKTVTGT NPVFAGANYA AWAVNVAQVI DSETADNLEK
```

```
         310        320        330        340        350        360
TTAALSILPG IGSVMGIADG AVHHNTEEIV AQSIALSSLM VAQAIPLVGE LVDIGFAAYN 370        380        390        400        410        420
FVESIINLFQ VVHNSYNRPA YSPGHKTQPF LPWGGGGSMH VAQPAVVLAN SRGVASFVCE 430        440        450        460        470        480
YGSAGKAAEV RVTVLRRAGS QMTEVCAATY TVEDELTFLD DSTCTGTSTE NKV*A*LTIQGL 490        500        510        520        530        540
RAVDTGLYIC KVELLYPPPY YVGM*A*GTQI YVIDPEPCPD SDGGGGSGGG GSGGGGSMHV 550        560        570        580        590        600
AQPAVVLANS RGVASFVCEY GSAGKAAEVR VTVLRRAGSQ MTEVCAATYT VEDELTFLDD 610        620        630        640        650        660
STCTGTSTEN KV*A*LTIQGLR AVDTGLYICK VELLYPPPYY VGM*A*GTQIY VIDPEPCPDS

DHHHHHH
```

3) DT390-bi-pCTLA-4-Non-N-Gly-6xHis (DNA sequence)
Underlined, DT390 domain. Double underlined, porcine CTLA-4 domain. Bold italics, mutated residues. Plain, BamHI recognition site and (G₄S)₃ linker (SEQ ID NO: 29)

GCT GGT GCT GAC

GACGTCGTCGACTCCTCCAAGTCCTTCGTCATGGAGAACTTCGCTTCCTAC

CACGGGACCAAGCCAGGTTACGTCGACTCCATCCAGAAGGGTATCCAGAA

GCCAAAGTCCGGCACCCAAGGTAACTACGACGACGACTGGAAGGGGTTCT

ACTCCACCGACAACAAGTACGACGCTGCGGGATACTCTGTAGATAATGAA

AACCCGCTCTCTGGAAAAGCTGGAGGCGTGGTCAAGGTCACCTACCCAGG

TCTGACTAAGGTCTTGGCTTTGAAGGTCGACAACGCTGAGACCATCAAGA

AGGAGTTGGGTTTGTCCTTGACTGAGCCATTGATGGAGCAAGTCGGTACC

GAAGAGTTCATCAAGAGATTCGGTGACGGTGCTTCCAGAGTCGTCTTGTC

CTTGCCATTCGCTGAGGGTTCTTCTAGCGTTGAATATATTAATAACTGGGA

ACAGGCTAAGGCTTTGTCTGTTGAATTGGAGATTAACTTCGAAACCAGAG

GTAAGAGAGGTCAAGATGCGATGTATGAGTATATGGCTCAAGCCTGTGCT

GGTAACAGAGTCAGACGTTCTGTTGGTTCCTCTTTGTCCTGTATCAACCTA

GACTGGGACGTCATCAGAGACAAGACTAAGACCAAGATCGAGTCTTTGAA

AGAGCATGGCCCAATCAAGAACAAGATGTCCGAATCCCCCGCTAAGACCG

TCTCCGAGGAAAAGGCCAAGCAATACCTAGAAGAGTTCCACCAAACCGCC

TTGGAGCATCCTGAATTGTCAGAACTTAAAACCGTTACTGGGACCAATCCT

GTATTCGCTGGGGCTAACTATGCGGCGTGGGCAGTAAACGTTGCGCAAGT

TATCGATAGCGAAACAGCTGATAATTTGGAAAAGACAACTGCTGCTCTTT

CGATACTTCCTGGTATCGGTAGCGTAATGGGCATTGCAGACGGTGCCGTTC

ACCACAATACAGAAGAGATAGTGGCACAATCCATCGCTTTGTCCTCTTTG

ATGGTTGCTCAAGCTATCCCATTGGTCGGTGAGTTGGTTGACATCGGTTTC

GCTGCCTACAACTTCGTCGAGTCCATCATCAACTTGTTCCAAGTCGTCCAC

AACTCCTACAACCGTCCGGCTTACTCCCCAGGTCACAAGACCCAACCATTC

TTG CCA TGG GGT GGT GGT GGT TCT ATG CAC GTT GCT CAA CCA GCT

GTT GTC TTG GCT AAC TCT

AGA GGT GTT GCT TCT TTC GTT TGT GAG TAC GGT TCT GCT GGT AAG

GCT GCT GAG GTT AGA GTT ACT GTT TTG AGA AGA GCT GGT TCT CAA

```
                           -continued
ATG ACT GAG GTT TGT GCT GCT ACT TAC ACT

GTT GAG GAC GAG TTG ACT TTC TTG GAC GAC TCT ACT TGT ACT GGT

ACT TCT ACT GAG AAC AAG GTT GCT TTG ACT ATT CAA GGT TTG AGA

GCT GTC GAC ACC GGT TTG TAC ATC TGT AAG

GTC GAA TTG TTG TAC CCA CCT CCA TAC TAC GTT GGT ATG GGT   GCT

GGT ACT CAA ATT TAC GTT ATT GAC CCT GAA CCA TGT CCT GAC TCT

GAC GGT GGT GGT GGT TCT GGT GGT GGT GGA TCC GGT GGT GGT GGT

TCT ATG CAC GTT

GCT CAA CCA GCT GTT GTC TTG GCT AAC TCT AGA GGT GTT GCT TCT

TTC GTT TGT GAG TAC GGT TCT GCT GGT AAG GCT GCT GAG GTT AGA

GTT ACT GTT TTG AGA AGA GCT GGT TCT CAA ATG ACT GAG GTT TGT

GCT GCT ACT TAC ACT GTT GAG GAC GAG TTG ACT TTC TTG GAC GAC

TCT ACT TGT ACT GGT ACT TCT ACT GAG AAC

AAG GTT GCT TTG ACT ATT CAA GGT TTG AGA GCT GTC GAC ACC GGT

TTG TAC ATC TGT AAG GTC GAA TTG TTG TAC CCA CCT CCA TAC TAC

GTT GGT ATG GGT GCT GGT ACT CAA ATT TAC GTT ATT GAC CCT GAA

CCA TGT CCT GAC TCT GAC CAC CAC CAC CAC CAC CAC
```

Example 5. Expression and Purification of the Porcine CTLA-4 Fusion Toxins

The recombinant porcine CTLA-4 fusion toxins were expressed using shaker flasks as described in Materials and Methods. Western blot analysis confirmed the expression using mouse anti-6×His monoclonal antibody. The secreted porcine CTLA-4 fusion toxin in the supernatant was captured directly by Ni-Sepharose Fast Flow Resin (FIGS. 9A, 10A and 11A). For the second step purification, a strong anion exchange resin Poros 50HQ was used. Sodium chloride alone did not work well for eluting the fusion toxin as the glycosylated yeast host protein was co-eluted with the fusion toxin (Woo et al 2003). Sodium borate was chosen as it would separate the fusion toxin from the glycosylated yeast host protein and the aggregates. However the maximal solubility for sodium borate is restricted to 200 mM, a concentration which is not strong enough to elute the majority of the fusion toxin. To overcome this problem, 50 mM NaCl was added to the 200 mM sodium borate elution buffer to increase the salt concentration. The majority of the fusion toxin was eluted with 200 mM sodium borate+50 mM NaCl (FIGS. 9B, 10B and 11B). After two step purification pure porcine CTLA-4 fusion toxins were obtained. The purity reached around 95%. The final purification yield was ~10 mg per liter of the original harvested supernatant.

Example 6. Protein Synthesis Inhibition Analysis for the Porcine CTLA-4 Fusion Toxins The cytotoxicity function of the porcine CTLA-4 fusion toxins were assessed by protein synthesis inhibition assay using a porcine CD80-expressing B-cell lymphoma cell line LCL13271-5E4. As shown in FIG. 12, DT390-pCTLA-4-Non-N-Gly is the best version to efficiently inhibit the protein synthesis in target cells. At a concentration of $1 \times 10^{-6}$ M, DT390-pCTLA-4-Non-N-Gly could still completely inhibit the protein synthesis. At concentration of $1 \times 10^{-8}$ M, it can still inhibit ⅓ of full protein synthesis. DT390-pCTLA-4-Gly is the worst version. Even at neat concentration ($2.63 \times 10^{-6}$ M). It can not completely inhibit protein synthesis. At concentration of $1 \times 10^{-6}$ M, it only inhibited about ⅔ of the full protein synthesis. DT390-bi-pCTLA-4-Non-N-Gly is a little bit worse than that of DT390-pCTLA-4-Non-N-Gly. Those data demonstrated that only the non-N-glycosylated porcine CTLA-4 derived version is fully functional and one non-N-glycosylated porcine CTLA-4 derived version is better than two non-N-glycosylated porcine CTLA-4 derived version.

Example 7. Binding Affinity of the Porcine CTLA-4 Fusion Toxins to Porcine CD80

Porcine CTLA-4 fusion toxins were biotinylated and the binding affinities to porcine CD80 were analyzed by flow cytometry using the porcine CD80-expressing B-cell lymphoma cell line (LC13271-5E4). As shown in FIGS. 13A-C, the $K_D$ value was determined by plotting the FACS-MFI values versus a wide range of concentrations of the porcine CTLA-4 fusion toxins. The non-linear least-squares curve fitting revealed a $K_D$ of 2 nM for DT390-pCTLA-4-Non-N-Gly, 4.7 nM for DT390-bi-pCTLA-4-Non-N-Gly and 17.3 nM for DT390-pCTLA-4-Gly (m3 value of the inset table in FIG. 13A-C). The $K_D$ values are well correlated to the protein synthesis inhibition function for each version of the fusion toxins. The binding affinity of DT390-pCTLA-4-Gly was decreased from 13 nM (pCTLA-4-Gly alone) to 17.3 nM. In contrast the binding affinity of DT390-pCTLA-4-Non-N-Gly improved from 13 nM (pCTLA-4-Non-N-Gly alone) to 2 nM. The binding affinity of DT390-bi-pCTLA-4-Non-N-Gly improved from 13 nM (pCTLA-4-Non-N-Gly alone) to 4.7 nM. In terms of the binding affinity, DT390-pCTLA-4-Non-N-Gly is also the best version.

To confirm the specific binding of the porcine CTLA-4 fusion toxins to porcine CD80, a dose-dependent blocking/competition assay for the binding of hamster anti-mouse CD80 mAb (clone 16-10A1) or biotinylated soluble porcine CTLA-4 to the porcine CD80 expressing B-cell lymphoma cell line (LCL13271-5E4) was also performed using non-biotinylated porcine CTLA-4 fusion toxins. The blocking/competition data reaffirmed the direct FACS binding analysis using biotinylated porcine CTLA-4 fusion toxins.

An in vivo functional study of DT390-pCTLA-4-Non-N-Gly using a porcine CD-80 expressing B-cell lymphoma mouse model was conducted. Administration of the DT390-pCTLA-4-Non-N-Gly delayed development of sickness caused by the cancer as compared with control animals.

Example 8. Human Non-N-Glycosylated CTLA-4 Proteins

Methods similar to those described above were used to create a human CTLA-4 protein. The codon-optimized non-N-glycosylated soluble human CTLA-4 DNA and amino acid sequence (aa36-161, 126 aa+6×His) was as follows:

```
                                       SEQ ID NO: 30
                                       SEQ ID NO: 31
aaggctatgcacgttgctcaaccagctgttgtcttggcttcttccagag
 K   A   M   H   V   A   Q   P   A   V   V   L   A   S   S   R
gtattgcttct
 G   I   A   S ttcgtttgtgagtacgcttctccaggtaaggctactgaggttagagtta
 F   V   C   E   Y   A   S   P   G   K   A   T   E   V   R   V
ctgtcttgaga
 T   V   L   R caagctgactctcaagttactgaggtttgtgctgctacttacatgatgg
 Q   A   D   S   Q   V   T   E   V   C   A   A   T   Y   M   M
gtaacgagttg
 G   N   E   L actttcttggacgactctatttgtactggtacttcttccggtaaccaag
 T   F   L   D   D   S   I   C   T   G   T   S   S   G   N   Q
ttgctttgact
 V   A   L   T attcaaggtttgagagctatggacactggtttgtacatttgtaaggttg
 I   Q   G   L   R   A   M   D   T   G   L   Y   I   C   K   V
agttgatgtac
 E   L   M   Y ccacctccatactacttgggtattggtgctggtactcaaatttacgtta
 P   P   P   Y   L   G   I   G   A   G   T   Q   I   Y   V
ttgacccagag
 I   D   P   E ccttgtccagactctgaccaccaccaccaccaccac
 P   C   P   D   S   D   H   H   H   H   H   H
```

The activity of the non-N-glycosylated human CTLA-4 fusion toxin was evaluated by a protein synthesis inhibition assay as described above. The protein was functional in this assay, though less so than the porcine version.

REFERENCES

Bour-Jordan, H., Esensten, J. H., Martinez-Llordella, M., Penaranda, C., Stumpf, M., Bluestone, J. A., 2011, Intrinsic and extrinsic control of peripheral T-cell tolerance by costimulatory molecules of the CD28/B7 family. Immunol Rev. 241, 180-205.

Brondyk, W. H., 2009, Selecting an appropriate method for expressing a recombinant protein. Methods Enzymol. 463, 131-147.

Cho, P. S., Lo, D. P., Wikiel, K. J., Rowland, H. C., Coburn, R. C., McMorrow, I. M., Goodrich, J. G., Arn, J. S., Billiter, R. A., Houser, S. L., Shimizu, A., Yang, Y. G., Sachs, D. H., Huang, C. A., 2007, Establishment of transplantable porcine tumor cell lines derived from MHC-inbred miniature swine. Blood, 110, 3996-4004.

Cregg, J. M., 2007, Introduction: distinctions between Pichia pastoris and other expression systems. Methods Mol Biol. 389, 1-10.

Garin, E. H., Mu, W., Arthur, J. M., Rivard, C. J., Araya, C. E., Shimada, M., Johnson, R. J., 2010, Urinary CD80 is elevated in minimal change disease but not in focal segmental glomerulosclerosis. Kidney Int. 78, 296-302.

Kim, G. B., Wang, Z., Liu, Y. Y., Stavrou, S., Mathias, A., Goodwin, K. J., Thomas, J. M., and Neville, D. M. Jr., 2007, A fold-back single-chain diabody format enhances the bioactivity of an anti-monkey CD3 recombinant diphtheria toxin-based immunotoxin. Protein Eng. Des. Sel. 20, 425-432.

Liu, Y. Y., Gordienko, I., Mathias, A., Ma, A., Thompson, J., Woo, J. H., and Neville, D. M. Jr., 2000, Expression of an anti-CD3 single-chain immunotoxin with a truncated diphtheria toxin in a mutant CHO cell line. Protein Expr. Purif. 19, 304-311.

Liu, Y. Y., Woo, J. H., and Neville, D. M. Jr., 2003, Targeted introduction of a diphtheria toxin resistant mutation into the chromosomal EF-2 locus of Pichia pastoris and expression of immunotoxin in the EF-2 mutants. Protein Expr. Purif. 30, 262-274.

Peraino, J., Zhang, H., Hermanrud, C. E., Li, G., Sachs, D. H., Christene A Huang, C. E., Wang, Z., 2012, Expression and purification of soluble porcine CTLA 4 in yeast Pichia pastoris. Protein Expr Purif 82:270-278.

Riha, P., Rudd, C. E., 2010, CD28 co-signaling in the adaptive immune response. Self. Nonself. 1, 231-240.

Rudd, C. E., Taylor, A., Schneider, H., 2009, CD28 and CTLA-4 coreceptor expression and signal transduction. Immunol Rev. 29, 12-26.

Sansom, D. M., 2000, CD28, CTLA-4 and their ligands: who does what and to whom? Immunology, 101, 169-177.

Sreekrishna, K., 1993, Strategies for optimizing protein expression and secretion in the methylotrophic yeast Pichia pastoris. In Industrial Microorganism: Basic and Applied Molecular Genetics. R. H. Baltz, G. D. Hegeman, and P. L. Skatrud, eds. American Society of Microbiology, Washington, D.C., pp. 119-126.

Van der Merwe, P. A., Bodian, D. L., Daenke, S., Linsley, P., Davis, S. J., 1997, CD80 (B7-1) binds both CD28 and CTLA-4 with a low affinity and very fast kinetics. J Exp Med. 185, 393-403.

Vaughan, A. N., Malde, P., Rogers, N. J., Jackson, I. M., Lechler, R. I., Dorling, A., 2000, Porcine CTLA4-Ig lacks a MYPPPY motif, binds inefficiently to human B7 and specifically suppresses human CD4+ T cell responses costimulated by pig but not human B7. J Immunol. 165, 3175-3181.

Wang, Z., Duran-Struuck, R., Crepeau, R., Matar, A., Hanekamp, I., Srinivasan, S., Neville, D. M., Sachs D. H., Huang C. A., 2011, Development of a Diphtheria Toxin Based Antiporcine CD3 Recombinant Immunotoxin. Bioconjug Chem. 22:2014-2020.

Wing, K., Onishi, Y., Prieto-Martin, P., Yamaguchi, T., Miyara, M., Fehervari, Z., Nomura, T., Sakaguchi, S., 2008, CTLA-4 control over Foxp3+ regulatory T cell function. Science, 322, 271-275.

Woo, J. H., and Neville Jr. D. M., 2003, Separation of bivalent anti-T cell immunotoxin from Pichia pastoris glycoproteins by borate anion exchange. BioTechniques 35, 392-398.

Woo, J. H., Liu, Y. Y., Mathias, A., Stavrou, S., Wang, Z., Thompson, J. Neville Jr. D. M., 2002, Gene optimization is necessary to express a bivalent anti-human anti-T cell immunotoxin in *Pichia pastoris*. Protein Expr. Purif. 25, 270-282.

Yamada, K, Yazawa, K., Shimizu, A., Iwanaga, T., Hisashi, Y., Nuhn, M., O'Malley, P., Nobori, S., Vagefi, P. A., Patience, C., Fishman, J., Cooper, D. K., Hawley, R. J., Greenstein, J., Schuurman, H. J., Awwad, M., Sykes, M., Sachs, D. H., 2005, Marked prolongation of porcine renal xenograft survival in baboons through the use of alpha1, 3-galactosyltransferase gene-knockout donors and the cotransplantation of vascularized thymic tissue. Nat. Med. 11, 32-34.

Zhu, S., Liu, S., Wan, L., Yang, G., Yang, H., Cheng, J., Lu, X., 2011, Molecular cloning, expression and characterization of the functional domain of CTLA4 from the rhesus monkey, *Macaca mulatta*. Dev Comp Immunol. 35:736-744.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion toxin comprising:

a first part comprising a cytotoxic protein, and a second part comprising a non-N-glycosylated human Cytotoxic T-Lymphocyte-Associated Protein 4 (CTLA4) comprising amino acids 39-152 of SEQ ID NO:1, wherein (i) the amino acid at position 113 is not Asparagine (N), and the amino acid at position 115 is neither Threonine (T) nor Serine (S); and (ii) the amino acid at position 145 is not Asparagine (N), and the amino acid at position 147 is neither Threonine (T) nor Serine (S).

2. The fusion toxin of claim 1, wherein the cytotoxic protein comprises diphtheria toxin, *Pseudomonas* exotoxin, or portions or variants thereof.

3. The fusion toxin of claim 1, further comprising a third part comprising a non-N-glycosylated human Cytotoxic T-Lymphocyte-Associated Protein 4 (CTLA4).

4. The fusion toxin of claim 1, further comprising a linker between the first and second parts.

5. A method of treating a subject who has an autoimmune disease, the method comprising administering to the subject a therapeutically effective amount of the fusion toxin of claim 1.

6. A method of treating transplant rejection a subject who has undergone or will undergo an organ transplantation procedure, the method comprising administering to the subject a therapeutically effective amount of the fusion toxin of claim 1.

7. A pharmaceutical composition comprising the fusion toxin of claim 1 and a physiologically acceptable carrier.

* * * * *

SEQUENCE LISTING

```
<160> NUMBER OF SEQ ID NOS: 31

<210> SEQ ID NO 1
<211> LENGTH: 174
<212> TYPE: PRT
<213> ORGANISM: Homo sapien

<400> SEQUENCE: 1

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Ala Lys Glu Lys Lys Pro Ser Tyr
145                 150                 155                 160

Asn Arg Gly Leu Cys Glu Asn Ala Pro Asn Arg Ala Arg Met
                165                 170

<210> SEQ ID NO 2
<211> LENGTH: 528
<212> TYPE: PRT
<213> ORGANISM: Artificial Sequence
<220> FEATURE:
<223> OTHER INFORMATION: DT390-pCTLA4-Non-N-Gly-6xHis

<400> SEQUENCE: 2

Ala Gly Ala Asp Asp Val Val Asp Ser Ser Lys Ser Phe Val Met Glu
 1               5                  10                  15

Asn Phe Ala Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
```

```
                 35                  40                  45
Asp Asp Trp Lys Gly Phe Tyr Ser Thr Asp Asn Lys Tyr Asp Ala Ala
 50                  55                  60
Gly Tyr Ser Val Asp Asn Glu Asn Pro Leu Ser Gly Lys Ala Gly Gly
 65                  70                  75                  80
Val Val Lys Val Thr Tyr Pro Gly Leu Thr Lys Val Leu Ala Leu Lys
                 85                  90                  95
Val Asp Asn Ala Glu Thr Ile Lys Lys Glu Leu Gly Leu Ser Leu Thr
                100                 105                 110
Glu Pro Leu Met Glu Gln Val Gly Thr Glu Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Ala Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
                370                 375                 380
His Lys Thr Gln Pro Phe Leu Pro Trp Gly Gly Gly Ser Met His
385                 390                 395                 400
Val Ala Gln Pro Ala Val Leu Ala Asn Ser Arg Gly Val Ala Ser
                405                 410                 415
Phe Val Cys Glu Tyr Gly Ser Ala Gly Lys Ala Ala Glu Val Arg Val
                420                 425                 430
Thr Val Leu Arg Arg Ala Gly Ser Gln Met Thr Glu Val Cys Ala Ala
                435                 440                 445
Thr Tyr Thr Val Glu Asp Glu Leu Thr Phe Leu Asp Asp Ser Thr Cys
                450                 455                 460
```

Thr Gly Thr Ser Thr Glu Asn Lys Val Ala Leu Thr Ile Gln Gly Leu
465                 470                 475                 480

Arg Ala Val Asp Thr Gly Leu Tyr Ile Cys Lys Val Glu Leu Leu Tyr
            485                 490                 495

Pro Pro Pro Tyr Tyr Val Gly Met Gly Ala Gly Thr Gln Ile Tyr Val
            500                 505                 510

Ile Asp Pro Glu Pro Cys Pro Asp Ser Asp His His His His His His
        515                 520                 525

<210> SEQ ID NO 3
<211> LENGTH: 667
<212> TYPE: PRT
<213> ORGANISM: Artificial Sequence
<220> FEATURE:
<223> OTHER INFORMATION: DT390-bi-pCTLA-4-Non-N-Gly-6xHis

<400> SEQUENCE: 3

Ala Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Lys Thr Gln Pro Phe Leu Pro Trp Gly Gly Gly Ser Met His
385                 390                 395                 400

Val Ala Gln Pro Ala Val Val Leu Ala Asn Ser Arg Gly Val Ala Ser
                405                 410                 415

Phe Val Cys Glu Tyr Gly Ser Ala Gly Lys Ala Ala Glu Val Arg Val
            420                 425                 430

Thr Val Leu Arg Arg Ala Gly Ser Gln Met Thr Glu Val Cys Ala Ala
        435                 440                 445

Thr Tyr Thr Val Glu Asp Glu Leu Thr Phe Leu Asp Asp Ser Thr Cys
    450                 455                 460

Thr Gly Thr Ser Thr Glu Asn Lys Val Ala Leu Thr Ile Gln Gly Leu
465                 470                 475                 480

Arg Ala Val Asp Thr Gly Leu Tyr Ile Cys Lys Val Glu Leu Leu Tyr
                485                 490                 495

Pro Pro Pro Tyr Tyr Val Gly Met Gly Ala Gly Thr Gln Ile Tyr Val
            500                 505                 510

Ile Asp Pro Glu Pro Cys Pro Asp Ser Asp Gly Gly Gly Ser Gly
        515                 520                 525

Gly Gly Gly Ser Gly Gly Gly Ser Met His Val Ala Gln Pro Ala
    530                 535                 540

Val Val Leu Ala Asn Ser Arg Gly Val Ala Ser Phe Val Cys Glu Tyr
545                 550                 555                 560

Gly Ser Ala Gly Lys Ala Ala Glu Val Arg Val Thr Val Leu Arg Arg
                565                 570                 575

Ala Gly Ser Gln Met Thr Glu Val Cys Ala Ala Thr Tyr Thr Val Glu
            580                 585                 590

Asp Glu Leu Thr Phe Leu Asp Asp Ser Thr Cys Thr Gly Thr Ser Thr
        595                 600                 605

Glu Asn Lys Val Ala Leu Thr Ile Gln Gly Leu Arg Ala Val Asp Thr
    610                 615                 620

Gly Leu Tyr Ile Cys Lys Val Glu Leu Leu Tyr Pro Pro Pro Tyr Tyr
625                 630                 635                 640

Val Gly Met Gly Ala Gly Thr Gln Ile Tyr Val Ile Asp Pro Glu Pro
                645                 650                 655

Cys Pro Asp Ser Asp His His His His His
            660                 665

<210> SEQ ID NO 4
<211> LENGTH: 528
<212> TYPE: PRT
<213> ORGANISM: Artificial Sequence
<220> FEATURE:
<223> OTHER INFORMATION: DT390-pCTLA-4-Gly-6xHis

<400> SEQUENCE: 4

```
Ala Gly Ala Asp Asp Val Val Asp Ser Ser Lys Ser Phe Val Met Glu
 1               5                  10                  15

Asn Phe Ala Ser Tyr His Gly Thr Lys Pro Gly Tyr Val Asp Ser Ile
             20                  25                  30

Gln Lys Gly Ile Gln Lys Pro Lys Ser Gly Thr Gln Gly Asn Tyr Asp
             35                  40                  45

Asp Asp Trp Lys Gly Phe Tyr Ser Thr Asp Asn Lys Tyr Asp Ala Ala
         50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
        210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr Gln Pro Phe Leu Pro Trp Gly Gly Gly Ser Met His
385                 390                 395                 400

Val Ala Gln Pro Ala Val Val Leu Ala Asn Ser Arg Gly Val Ala Ser
                405                 410                 415
```

```
Phe Val Cys Glu Tyr Gly Ser Ala Gly Lys Ala Ala Glu Val Arg Val
            420                 425                 430

Thr Val Leu Arg Arg Ala Gly Ser Gln Met Thr Glu Val Cys Ala Ala
        435                 440                 445

Thr Tyr Thr Val Glu Asp Glu Leu Thr Phe Leu Asp Asp Ser Thr Cys
    450                 455                 460

Thr Gly Thr Ser Thr Glu Asn Lys Val Asn Leu Thr Ile Gln Gly Leu
465                 470                 475                 480

Arg Ala Val Asp Thr Gly Leu Tyr Ile Cys Lys Val Glu Leu Leu Tyr
                485                 490                 495

Pro Pro Pro Tyr Tyr Val Gly Met Gly Asn Gly Thr Gln Ile Tyr Val
            500                 505                 510

Ile Asp Pro Glu Pro Cys Pro Asp Ser Asp His His His His His His
        515                 520                 525
```

<210> SEQ ID NO 5
<211> LENGTH: 8
<212> TYPE: PRT
<213> ORGANISM: Artificial Sequence
<220> FEATURE:
<223> OTHER INFORMATION: synthetically generated peptides

<400> SEQUENCE: 5

```
Asp Tyr Lys Asp Asp Asp Asp Lys
1               5
```

<210> SEQ ID NO 6
<211> LENGTH: 6
<212> TYPE: PRT
<213> ORGANISM: Artificial Sequence
<220> FEATURE:
<223> OTHER INFORMATION: synthetically generated peptides

<400> SEQUENCE: 6

```
Tyr Pro Tyr Asp Val Pro
1               5
```

<210> SEQ ID NO 7
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 7

```
Ile Leu Lys Lys Ala Thr Ala Tyr Ile Leu
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: synthetically generated peptides

<400> SEQUENCE: 8

```
Glu Gln Lys Leu Ile Ser Glu Glu Asp Leu
1               5                   10
```

<210> SEQ ID NO 9
<211> LENGTH: 57
<212> TYPE: DNA
<213> ORGANISM: Artificial Sequence
<220> FEATURE:

<223> OTHER INFORMATION: synthetically generated PCR primers

<400> SEQUENCE: 9
ccgctcgaga agagagaggc tgaagctatg cacgttgctc aaccagctgt tgtcttg    57

<210> SEQ ID NO 10
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 10
accgtactca caaacgaaag aagcaacacc tctagagtta gccaagacaa cagctggttg    60
agc    63

<210> SEQ ID NO 11
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 11
tctttcgttt gtgagtacgg ttctgctggt aaggctgctg aggttagagt tactgttttg    60
aga    63

<210> SEQ ID NO 12
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 12
gtaagtagca gcacaaacct cagtcatttg agaaccagct cttctcaaaa cagtaactct    60
aac    63

<210> SEQ ID NO 13
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 13
gaggtttgtg ctgctactta cactgttgag gacgagttga ctttcttgga cgactctact    60
tgt    63

<210> SEQ ID NO 14
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 14
ttgaatagtc aagttaacct tgttctcagt agaagtacca gtacaagtag agtcgtccaa    60
gaa    63

<210> SEQ ID NO 15
<211> LENGTH: 63

<212> TYPE: DNA
<213> ORGANISM: Artificial Sequence
<220> FEATURE:
<223> OTHER INFORMATION: synthetically generated PCR primers

<400> SEQUENCE: 15
aaggttaact tgactattca aggtttgaga gctgtcgaca ccggtttgta catctgtaag    60
gtc                                                                 63

<210> SEQ ID NO 16
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 16
gttacccata ccaacgtagt atggaggtgg gtacaacaat tcgaccttac agatgtacaa    60
acc                                                                 63

<210> SEQ ID NO 17
<211> LENGTH: 63
<212> TYPE: DNA
<213> ORGANISM: Artificial Sequence
<220> FEATURE:
<223> OTHER INFORMATION: synthetically generated PCR primers

<400> SEQUENCE: 17
tactacgttg gtatgggtaa cggtactcaa atttacgtta ttgaccctga accatgtcct    60
gac                                                                 63

<210> SEQ ID NO 18
<211> LENGTH: 57
<212> TYPE: DNA
<213> ORGANISM: Artificial Sequence
<220> FEATURE:
<223> OTHER INFORMATION: synthetically generated PCR primers

<400> SEQUENCE: 18
ccggaattct tagtggtggt ggtggtggtg gtcagagtca ggacatggtt cagggtc       57

<210> SEQ ID NO 19
<211> LENGTH: 45
<212> TYPE: DNA
<213> ORGANISM: Artificial Sequence
<220> FEATURE:
<223> OTHER INFORMATION: synthetically generated PCR primers

<400> SEQUENCE: 19
acttctactg agaacaaggt tgctttgact attcaaggtt tgaga                    45

<210> SEQ ID NO 20
<211> LENGTH: 45
<212> TYPE: DNA
<213> ORGANISM: Artificial Sequence
<220> FEATURE:
<223> OTHER INFORMATION: synthetically generated PCR primers

<400> SEQUENCE: 20
tctcaaacct tgaatagtca aagcaacctt gttctcagta gaagt                    45

<210> SEQ ID NO 21
<211> LENGTH: 45
<212> TYPE: DNA

<213> ORGANISM: Artificial Sequence
<220> FEATURE:
<223> OTHER INFORMATION: synthetically generated PCR primers

<400> SEQUENCE: 21
ccatactacg ttggtatggg tgctggtact caaatttacg ttatt    45

<210> SEQ ID NO 22
<211> LENGTH: 45
<212> TYPE: DNA
<213> ORGANISM: Artificial Sequence
<220> FEATURE:
<223> OTHER INFORMATION: synthetically generated PCR primers

<400> SEQUENCE: 22
aataacgtaa atttgagtac cagcacccat accaacgtag tatgg    45

<210> SEQ ID NO 23
<211> LENGTH: 390
<212> TYPE: DNA
<213> ORGANISM: Artificial Sequence
<220> FEATURE:
<223> OTHER INFORMATION: codon optimized pCTLA-4

<400> SEQUENCE: 23
atgcacgttg ctcaaccagc tgttgtcttg gctaactcta gaggtgttgc ttctttcgtt    60
tgtgagtacg gttctgctgg taaggctgct gaggttagag ttactgtttt gagaagagct   120
ggttctcaaa tgactgaggt ttgtgctgct acttacactg ttgaggacga gttgactttc   180
ttggacgact ctacttgtac tggtacttct actgagaaca aggttaactt gactattcaa   240
ggtttgagag ctgtcgacac cggttttgtac atctgtaagg tcgaattgtt gtacccacct   300
ccatactacg ttggtatggg taacggtact caaatttacg ttattgaccc tgaaccatgt   360
cctgactctg accaccacca ccaccaccac                                    390

<210> SEQ ID NO 24
<211> LENGTH: 130
<212> TYPE: PRT
<213> ORGANISM: Artificial Sequence
<220> FEATURE:
<223> OTHER INFORMATION: porcine CTLA-4

<400> SEQUENCE: 24

Met His Val Ala Gln Pro Ala Val Val Leu Ala Asn Ser Arg Gly Val
 1               5                  10                  15

Ala Ser Phe Val Cys Glu Tyr Gly Ser Ala Gly Lys Ala Ala Glu Val
            20                  25                  30

Arg Val Thr Val Leu Arg Arg Ala Gly Ser Gln Met Thr Glu Val Cys
        35                  40                  45

Ala Ala Thr Tyr Thr Val Glu Asp Glu Leu Thr Phe Leu Asp Asp Ser
    50                  55                  60

Thr Cys Thr Gly Thr Ser Thr Glu Asn Lys Val Asn Leu Thr Ile Gln
65                  70                  75                  80

Gly Leu Arg Ala Val Asp Thr Gly Leu Tyr Ile Cys Lys Val Glu Leu
                85                  90                  95

Leu Tyr Pro Pro Pro Tyr Val Gly Met Gly Asn Gly Thr Gln Ile
            100                 105                 110

Tyr Val Ile Asp Pro Glu Pro Cys Pro Asp Ser Asp His His His
        115                 120                 125

His His

<210> SEQ ID NO 25
<211> LENGTH: 390
<212> TYPE: DNA
<213> ORGANISM: Artificial Sequence
<220> FEATURE:
<223> OTHER INFORMATION: codon optimized mutant pCTLA-4

<400> SEQUENCE: 25

```
atgcacgttg ctcaaccagc tgttgtcttg gctaactcta gaggtgttgc ttctttcgtt      60
tgtgagtacg gttctgctgg taaggctgct gaggttagag ttactgtttt gagaagagct     120
ggttctcaaa tgactgaggt ttgtgctgct acttacactg ttgaggacga gttgactttc     180
ttggacgact ctacttgtac tggtacttct actgagaaca aggttgcttt gactattcaa     240
ggtttgagag ctgtcgacac cggttttgtac atctgtaagg tcgaattgtt gtacccacct    300
ccatactacg ttggtatggg tgctggtact caaatttacg ttattgaccc tgaaccatgt     360
cctgactctg accaccacca ccaccaccac                                      390
```

<210> SEQ ID NO 26
<211> LENGTH: 130
<212> TYPE: PRT
<213> ORGANISM: Artificial Sequence
<220> FEATURE:
<223> OTHER INFORMATION: mutant pCTLA4

<400> SEQUENCE: 26

```
Met His Val Ala Gln Pro Ala Val Val Leu Ala Asn Ser Arg Gly Val
  1               5                  10                  15

Ala Ser Phe Val Cys Glu Tyr Gly Ser Ala Gly Lys Ala Ala Glu Val
             20                  25                  30

Arg Val Thr Val Leu Arg Arg Ala Gly Ser Gln Met Thr Glu Val Cys
         35                  40                  45

Ala Ala Thr Tyr Thr Val Glu Asp Glu Leu Thr Phe Leu Asp Asp Ser
     50                  55                  60

Thr Cys Thr Gly Thr Ser Thr Glu Asn Lys Val Ala Leu Thr Ile Gln
 65                  70                  75                  80

Gly Leu Arg Ala Val Asp Thr Gly Leu Tyr Ile Cys Lys Val Glu Leu
                 85                  90                  95

Leu Tyr Pro Pro Pro Tyr Tyr Val Gly Met Gly Ala Gly Thr Gln Ile
            100                 105                 110

Tyr Val Ile Asp Pro Glu Pro Cys Pro Asp Ser Asp His His His His
        115                 120                 125

His His
    130
```

<210> SEQ ID NO 27
<211> LENGTH: 1584
<212> TYPE: DNA
<213> ORGANISM: Artificial Sequence
<220> FEATURE:
<223> OTHER INFORMATION: DT390-pCTLA-4-Gly-6xHis

<400> SEQUENCE: 27

```
gctggtgctg acgacgtcgt cgactcctcc aagtccttcg tcatggagaa cttcgcttcc      60
taccacggga ccaagccagg ttacgtcgac tccatccaga gggtatcca gaagccaaag     120 tccggcaccc aaggtaacta cgacgacgac tggaaggggt tctactccac cgacaacaag     180
```

```
tacgacgctg cgggatactc tgtagataat gaaaacccgc tctctggaaa agctggaggc    240
gtggtcaagg tcacctaccc aggtctgact aaggtcttgg cttttgaaggt cgacaacgct   300 gagaccatca agaaggagtt gggtttgtcc ttgactgagc cattgatgga gcaagtcggt   360
accgaagagt tcatcaagag attcggtgac ggtgcttcca gagtcgtctt gtccttgcca   420
ttcgctgagg gttcttctag cgttgaatat attaataact gggaacaggc taaggctttg   480
tctgttgaat tggagattaa cttcgaaacc agaggtaaga gaggtcaaga tgcgatgtat   540
gagtatatgg ctcaagcctg tgctggtaac agagtcagac gttctgttgg ttcctctttg   600
tcctgtatca acctagactg ggacgtcatc agagacaaga ctaagaccaa gatcgagtct   660
ttgaaagagc atggcccaat caagaacaag atgtccgaat cccccgctaa gaccgtctcc   720
gaggaaaagg ccaagcaata cctagaagag ttccaccaaa ccgccttgga gcatcctgaa   780
ttgtcagaac ttaaaaccgt tactgggacc aatcctgtat tcgctggggc taactatgcg   840
gcgtgggcag taaacgttgc gcaagttatc gatagcgaaa cagctgataa tttggaaaag   900
acaactgctg ctctttcgat acttcctggt atcggtagcg taatgggcat gcagacggt    960 gccgttcacc acaatacaga agagatagtg cacaatcca tcgctttgtc ctctttgatg   1020
gttgctcaag ctatcccatt ggtcggtgag ttggttgaca tcggtttcgc tgcctacaac   1080
ttcgtcgagt ccatcatcaa cttgttccaa gtcgtccaca actcctacaa ccgtccggct   1140
tactccccag gtcacaagac ccaaccattc ttgccatggg gtggtggtgg ttctatgcac   1200
gttgctcaac cagctgttgt cttggctaac tctagaggtg ttgcttcttt cgtttgtgag   1260 tacgttctc tggtaaggc tgctgaggtt agagttactg ttttgagaag agctggttct   1320
caaatgactg aggtttgtgc tgctacttac actgttgagg acgagttgac tttcttggac   1380
gactctactt gtactggtac ttctactgag aacaaggtta acttgactat tcaaggtttg   1440
agagctgtcg acaccggttt gtacatctgt aaggtcgaat tgttgtaccc acctccatac   1500
tacgttggta tgggtaacgg tactcaaatt tacgttattg accctgaacc atgtcctgac   1560
tctgaccacc accaccacca ccac                                          1584
```

<210> SEQ ID NO 28
<211> LENGTH: 1578
<212> TYPE: DNA
<213> ORGANISM: Artificial Sequence
<220> FEATURE:
<223> OTHER INFORMATION: DT390-pCTLA4-Non-N-Gly-6xHis

<400> SEQUENCE: 28

```
gctggtgctg acgacgtcgt cgactcctcc aagtccttcg tcatggagaa cttcgcttcc    60
taccacggga ccaagccagg ttacgtcgac tccatccaga agggtatcca gaagccaaag   120
tccggcaccc aaggtaacta cgacgacgac tggaaggggt tctactccac cgacaacaag   180
tacgacgctg cgggatactc tgtagataat gaaaacccgc tctctggaaa agctggaggc   240
gtggtcaagg tcacctaccc aggtctgact aaggtcttgg cttttgaaggt cgacaacgct   300 gagaccatca agaaggagtt gggtttgtcc ttgactgagc cattgatgga gcaagtcggt   360
accgaagagt tcatcaagag attcggtgac ggtgcttcca gagtcgtctt gtccttgcca   420
ttcgctgagg gttcttctag cgttgaatat attaataact gggaacaggc taaggctttg   480
tctgttgaat tggagattaa cttcgaaacc agaggtaaga gaggtcaaga tgcgatgtat   540
gagtatatgg ctcaagcctg tgctggtaac agagtcagac gttctgttgg ttcctctttg   600
tcctgtatca acctagactg ggacgtcatc agagacaaga ctaagaccaa gatcgagtct   660
```

```
ttgaaagagc atggcccaat caagaacaag atgtccgaat cccccgctaa gaccgtctcc    720
gaggaaaagg ccaagcaata cctagaagag ttccaccaaa ccgccttgga gcatcctgaa    780
ttgtcagaac ttaaaaccgt tactgggacc aatcctgtat tcgctggggc taactatgcg    840
gcgtgggcag taaacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg gcacaatcca tcgctttgtc ctctttgatg   1020
gttgctcaag ctatcccatt ggtcggtgag ttggttgaca tcggtttcgc tgcctacaac   1080
ttcgtcgagt ccatcatcaa cttgttccaa gtcgtccaca actcctacaa ccgtccggct   1140
tactccccag gtcacaagac ccaaccattc ttgggtggtg gtggttctat gcacgttgct   1200
caaccagctg ttgtcttggc taactctaga ggtgttgctt ctttcgtttg tgagtacggt   1260
tctgctggta aggctgctga ggttagagtt actgttttga agagctgg ttctcaaatg    1320 actgaggttt gtgctgctac ttacactgtt gaggacgagt tgactttctt ggacgactct   1380
acttgtactg gtacttctac tgagaacaag gttgctttga ctattcaagg tttgagagct   1440
gtcgacaccg gtttgtacat ctgtaaggtc gaattgttgt acccacctcc atactacgtt   1500
ggtatgggtg ctggtactca aatttacgtt attgaccctg aaccatgtcc tgactctgac   1560
caccaccacc accaccac                                                 1578

<210> SEQ ID NO 29
<211> LENGTH: 2001
<212> TYPE: DNA
<213> ORGANISM: Artificial Sequence
<220> FEATURE:
<223> OTHER INFORMATION: DT390-bi-pCTLA-4-Non-N-Gly-6xHis

<400> SEQUENCE: 29
gctggtgctg acgacgtcgt cgactcctcc aagtccttcg tcatggagaa cttcgcttcc     60
taccacggga ccaagccagg ttacgtcgac tccatccaga agggtatcca gaagccaaag    120
tccggcaccc aagtaactac gacgacgac tggaagggt tctactccac cgacaacaag    180
tacgacgctg cgggatactc tgtagataat gaaaacccgc tctctggaaa agctggaggc    240
gtggtcaagg tcacctaccc aggtctgact aaggtcttgg ctttgaaggt cgacaacgct    300
gagaccatca gaaggagtt gggttttgtcc ttgactgagc cattgatgga gcaagtcggt    360
accgaagagt tcatcaagag attcggtgac ggtgcttcca gagtcgtctt gtccttgcca    420
ttcgctgagg gttcttctag cgttaatat attaataact gggaacaggc taaggctttg    480
tctgttgaat tggagattaa cttcgaaacc agaggtaaga gaggtcaaga tgcgatgtat    540
gagtatatgc tcaagcctg tgctggtaac agagtcagac gttctgttgg ttcctctttg    600
tcctgtatca acctagactg ggacgtcatc agagacaaga ctaagaccaa gatcgagtct    660
ttgaaagagc atggcccaat caagaacaag atgtccgaat cccccgctaa gaccgtctcc    720
gaggaaaagg ccaagcaata cctagaagag ttccaccaaa ccgccttgga gcatcctgaa    780
ttgtcagaac ttaaaaccgt tactgggacc aatcctgtat tcgctggggc taactatgcg    840
gcgtgggcag taaacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg gcacaatcca tcgctttgtc ctctttgatg   1020
gttgctcaag ctatcccatt ggtcggtgag ttggttgaca tcggtttcgc tgcctacaac   1080
```

```
ttcgtcgagt ccatcatcaa cttgttccaa gtcgtccaca actcctacaa ccgtccggct    1140
tactccccag gtcacaagac ccaaccattc ttgccatggg gtggtggtgg ttctatgcac    1200
gttgctcaac cagctgttgt cttggctaac tctagaggtg ttgcttcttt cgtttgtgag    1260
tacggttctg ctggtaaggc tgctgaggtt agagttactg ttttgagaag agctggttct    1320
caaatgactg aggtttgtgc tgctacttac actgttgagg acgagttgac tttcttggac    1380
gactctactt gtactggtac ttctactgag aacaaggttg ctttgactat tcaaggtttg    1440
agagctgtcg acaccggttt gtacatctgt aaggtcgaat tgttgtaccc acctccatac    1500
tacgttggta tgggtgctgg tactcaaatt tacgttattg accctgaacc atgtcctgac    1560
tctgacggtg gtggtggttc tggtggtggt ggatccggtg gtggtggttc tatgcacgtt    1620
gctcaaccag ctgttgtctt ggctaactct agaggtgttg cttctttcgt tgtgagtac    1680 ggttctgctg gtaaggctgc tgaggttaga gttactgttt tgagaagagc tggttctcaa    1740
atgactgagg tttgtgctgc tacttacact gttgaggacg agttgacttt cttggacgac    1800
tctacttgta ctggtacttc tactgagaac aaggttgctt tgactattca aggtttgaga    1860
gctgtcgaca ccggtttgta catctgtaag gtcgaattgt tgtacccacc tccatactac    1920
gttggtatgg gtgctggtac tcaaatttac gttattgacc ctgaaccatg tcctgactct    1980
gaccaccacc accaccacca c                                              2001

<210> SEQ ID NO 30
<211> LENGTH: 396
<212> TYPE: DNA
<213> ORGANISM: Artificial Sequence
<220> FEATURE:
<223> OTHER INFORMATION: codon optimized Non-gly-Human CTLA-4-6His

<400> SEQUENCE: 30
aaggctatgc acgttgctca accagctgtt gtcttggctt cttccagagg tattgcttct      60
ttcgtttgtg agtacgcttc tccaggtaag gctactgagg ttagagttac tgtcttgaga     120
caagctgact ctcaagttac tgaggtttgt gctgctactt acatgatggg taacgagttg     180
actttcttgg acgactctat tgtactggt acttcttccg gtaaccaagt tgctttgact      240
attcaaggtt tgagagctat ggacactggt ttgtacattt gtaaggttga gttgatgtac     300
ccacctccat actacttggg tattggtgct ggtactcaaa tttacgttat tgacccagag     360
ccttgtccag actctgacca ccaccaccac caccac                               396

<210> SEQ ID NO 31
<211> LENGTH: 132
<212> TYPE: PRT
<213> ORGANISM: Artificial Sequence
<220> FEATURE:
<223> OTHER INFORMATION: Non-gly-Human CTLA-4-6His

<400> SEQUENCE: 31

Lys Ala Met His Val Ala Gln Pro Ala Val Val Leu Ala Ser Ser Arg
  1               5                  10                  15

Gly Ile Ala Ser Phe Val Cys Glu Tyr Ala Ser Pro Gly Lys Ala Thr
             20                  25                  30

Glu Val Arg Val Thr Val Leu Arg Gln Ala Asp Ser Gln Val Thr Glu
         35                  40                  45

Val Cys Ala Ala Thr Tyr Met Met Gly Asn Glu Leu Thr Phe Leu Asp
     50                  55                  60

Asp Ser Ile Cys Thr Gly Thr Ser Ser Gly Asn Gln Val Ala Leu Thr
```

-continued

```
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Ala Gly Thr
            100                 105                 110

Gln Ile Tyr Val Ile Asp Pro Glu Pro Cys Pro Asp Ser Asp His His
        115                 120                 125

His His His His
    130
```